(12) United States Patent
Udvardi et al.

(10) Patent No.: US 8,907,164 B2
(45) Date of Patent: Dec. 9, 2014

(54) REGULATING NUTRIENT ALLOCATION IN PLANTS

(75) Inventors: Michael Udvardi, Ardmore, OK (US); Jiading Yang, Ardmore, OK (US); Eric Worley, Gordonville, TX (US)

(73) Assignee: The Samuel Roberts Noble Foundations, Inc., Ardmore, OK (US)

( * ) Notice: Subject to any disclaimer, the term of this patent is extended or adjusted under 35 U.S.C. 154(b) by 516 days.

(21) Appl. No.: 13/090,114

(22) Filed: Apr. 19, 2011

(65) Prior Publication Data

US 2011/0271398 A1  Nov. 3, 2011

Related U.S. Application Data

(60) Provisional application No. 61/325,795, filed on Apr. 19, 2010.

(51) Int. Cl.
| | | |
|---|---|---|
| *C12N 15/82* | (2006.01) | |
| *C12N 15/63* | (2006.01) | |
| *A01H 1/06* | (2006.01) | |
| *C12N 15/29* | (2006.01) | |
| *C07K 14/415* | (2006.01) | |

(52) U.S. Cl.
CPC .......... *C12N 15/8261* (2013.01); *C07K 14/415* (2013.01)
USPC ........... 800/290; 800/278; 800/287; 800/295; 435/91.4; 435/69.1; 435/419; 435/468; 536/23.6; 530/370

(58) Field of Classification Search
None
See application file for complete search history.

(56) References Cited

U.S. PATENT DOCUMENTS

| 7,060,875 B2 | 6/2006 | Lim et al. |
| 7,820,882 B2 | 10/2010 | Dubcovsky et al. |
| 2009/0288218 A1 | 11/2009 | Gan et al. |

FOREIGN PATENT DOCUMENTS

| WO | WO/2004/108931 | 12/2004 | |
| WO | WO 2008069878 | * 6/2008 | ............. C12N 15/29 |

OTHER PUBLICATIONS

McClean et al (NDSU, 1998).*
Olsen et al (Trends in Plant Science, 10(2), pp. 79-87, 2005).*
Guo et al (The Plant Journal, 46, pp. 601-612, 2006).*
Guo et al (Plant, Cell, and Environment, 27, pp. 521-549, 2004).*
Thimm et al., "MAPMAN: a user-driven tool to display genomics data sets onto diagrams of metabolic pathways and other biological processes," *Plant J.*, 37:914-39, 2004.
Sperotto et al., "Identification of up-regulated genes in flag leaves during rice grain filling and characterization of *Os*NAC5, a new ABA-dependent transcription factor," *Planta*, 230:985, 2009.
Gou et al., "AtNAP, a NAC family transcription factor, has an important role in leaf senescence," *Plant J.*, 46:601-612, 2006.
Von Arnim et al., "Cloning vectors for the expression of green fluorescent proteins in transgenic plants," *Gene*, 221:35, 1998.
Zuo et al., "An estrogen receptor-based transactivator XVE mediates highly inducible gene expression in transgenic plants," *Plant J.*, 24:265, 2000.

* cited by examiner

*Primary Examiner* — Anne Kubelik
*Assistant Examiner* — Stephen Uyeno
(74) *Attorney, Agent, or Firm* — Dentons US LLP

(57) ABSTRACT

The invention provides coding and promoter sequences for a VS-1 and AP-2 gene, which affects the developmental process of senescence in plants. Vectors, transgenic plants, seeds, and host cells comprising heterologous VS-1 and AP-2 genes are also provided. Additionally provided are methods of altering nutrient allocation and composition in a plant using the VS-1 and AP-2 genes.

28 Claims, 13 Drawing Sheets c

FIG. 4 a

```
VS-1    MTSST-RLPNLPAGFRFHPTDEELIVHYLMNQASSIPCPVPIVAEVNIYQCNPWDLPAKA  59
AP-2    MPSATSRLPNLPAGFRFHPTDEELIVHYLMNQASSLPCPVPIIAEVNIYQCNPWDLPAKA  60
AtNAP   MEVTS--QSTLPPGFRFHPTDEELIVYYLRNQTMSKPCPVSIIPEVDIYKFDPWQLPEKT  58
          * ::   ..**.***************:** **: * ****.*:.**:**: :**:** *:

VS-1    LFGENEWYFFSPRDRKYPNGARPNRAAGSGYWKATGTDKAILLTPTSENIGVKKALVFYG 119
AP-2    LFGENEWYFFSPRDRKYPNGARPNRAAGSGYWKATGTDKAILLTPTSENIGVKKALVFYG 120
AtNAP   EFGENEWYFFSPRERKYPNGVRPNRAAVSGYWKATGTDKAIHSG--SSNVGVKKALVFYK 116
         ************:****** ****** ************** .   *.*:*********

VS-1    GKPPKGVKTDWIMHEYRLTGANKNTKRRGSSMRLDDWVLCRIHKKSNNFQLSDQDQEGST 179
AP-2    GKPPKGVKTDWIMHEYRLTGANKTTKRRGSSMRLDDWVLCRIHKKSNNFQFSDKDQEGST 180
AtNAP   GRPPKGIKTDWIMHEYRLHDSRKASTKRNGSMRLDEWVLCRIYKKRGASKLLN-EQEG-- 173
        *:****:***********  .:.* :::*..*****:****** :**:.   :: :.***

VS-1    VEEE-SLNN-KMNVTITASPKSEANNDGHDHQFHPT--TMAMNKSYSITDLLNTIDYSAL 235
AP-2    VEEEESLNNNMMNGTIAASPKSEAN-DDHDHQFHPTTMTMTMSKSYSITDLLNTIDYSAL 239
AtNAP   -----FMDEVLMEDETKVVVN-EAERRTEEEIMMMT--SMKLPRTCSLAHLL-EMDYMGP 224
             ::: *:   .  : **:   .:. :  *  :*  : : ::*::.**  :** .

VS-1    SQFLDAPAEPEPPLIYPTTTQTHHEALLNYNNYVNNSHFNLPQVDAYSDHVATNCNGLKR 295
AP-2    SQLLDAPAEPEPPLIYPITTQT-HESLLSYNN--DSHYFNLPQVDACSDHVAPNCNGLKR 296
AtNAP   VSHID-------------------------------NFSQFD------------------ 235
         . :*                                *:.*.*

VS-1    KRVMTMDGAESS-FDDDGSSNFSRKLLKLPSDS-RSSSHSHFGSTTSSYCN-QQLVDTSG 352
AP-2    KRVMTMDGAESSALDGSSSSNFSRK-LKLPSDSIRSSSHSHFGSTTSSYCNQQQLVDRSG 355
AtNAP   ---------------------------------------HLHQPDSESSWFGDLQFNQDEI 257
                                                 * *  .: **:   *: : .

VS-1    FQYSSVLSYPFLEMQ 367
AP-2    FQYSSLLSYPFLEMQ 370
AtNAP   LNHHRQAMFKF---- 268
        :::      : *
``` a b

REGULATING NUTRIENT ALLOCATION IN PLANTS

This application claims the priority of U.S. Provisional Appl. Ser. No. 61/325,795 filed Apr. 19, 2010, the entire disclosure of which is incorporated herein by reference.

STATEMENT REGARDING FEDERALLY SPONSORED RESEARCH OR DEVELOPMENT

The disclosed subject matter was developed in part with funding from the Department of Energy BioEnergy Science Center grant number DE-PS02-06ER64304. The government may have certain rights in the invention.

INCORPORATION OF SEQUENCE LISTING

The sequence listing that is contained in the file named "NBLE071US_ST25.txt", which is 38,943 bytes (measured in MS-WINDOWS) and was created on Apr. 19, 2011, is filed herewith by electronic submission and incorporated herein by reference.

BACKGROUND OF THE INVENTION

1. Field of the Invention

The present invention relates generally to the field of molecular biology. More specifically, the invention relates to plant genes involved in plant senescence and methods of use thereof.

2. Description of the Related Art

Modifying the distribution of one or more nutrients within a plant, for example by altering leaf senescence processes, may be beneficial by directing such nutrients to harvested organs such as seeds, roots, tubers, or leaves. In nature, nutrient remobilization from shoots to roots during seasonal senescence of shoots conserves nutrients in perennial plants. In cultivated crops, nutrient redistribution from leaves to roots prior to harvest of a plant's aerial tissues can provide beneficial results, such as a lowered requirement for input of fertilizer in the following crop cycle. Such nutrient redistribution could be important for sustainable production of biomass for biofuels. Nutrient redistribution from leaves to seeds prior to the harvest of the seeds could result in improved seed quality and/or nutrient content.

NAM/ATAF1,2/CUC2 ("NAC") transcription factors have been implicated in a wide range of plant processes including hormonal signaling, meristem initiation and maintenance, root system development, and environmental responses. It has been unclear which genes are regulated by NAC TFs for instance to trigger nutrient redistribution, and genes regulating leaf senescence in crops important for biofuel production have yet to be identified. The present invention provides such genes.

SUMMARY OF THE INVENTION

In one aspect, the invention provides a polynucleotide molecule comprising a sequence selected from the group consisting of: (a) a sequence encoding a polypeptide at least 85% identical to SEQ ID NO:2 or 4, wherein the polypeptide regulates plant leaf senescence; (b) a sequence comprising SEQ ID NO:1 or 3; (c) a sequence hybridizing to (b) under wash conditions of 0.15 M NaCl and 70° C. for 10 minutes, wherein the sequence encodes a protein that regulates plant leaf senescence; (d) a sequence comprising at least 85% sequence identity over the full length of the SEQ ID NO:1 or 3, wherein the sequence encodes a protein that regulates plant leaf senescence; and (e) a sequence complementary to (a), (b), (c) or (d). In one embodiment, the polynucleotide molecule comprises the sequence of SEQ ID NO:1 or SEQ ID NO:3.

Another aspect of the invention relates to a recombinant vector comprising such a polynucleotide molecule, operably linked to a heterologous promoter functional in plants. In certain embodiments, the recombinant vector may further comprise at least one additional sequence chosen from the group consisting of: a regulatory sequence, a selectable marker, a leader sequence and a terminator. In certain embodiments the additional sequence of the recombinant vector may be a heterologous sequence. In other embodiments, the recombinant vector may comprise a promoter which is a tissue-specific promoter, such as one that directs expression in leaf tissue. In another embodiment, the recombinant vector of may be defined as an isolated expression cassette.

In another aspect, the invention provides a polypeptide selected from the group consisting of: (a) a polypeptide comprising the amino acid sequence of SEQ ID NO:2 or 4; and (b) a polypeptide having at least 85% sequence identity to SEQ ID NO:2 or 4, wherein the polypeptide regulates plant leaf senescence. In some embodiments the polypeptide comprises the amino acid sequence of SEQ ID NO:2.

A further aspect of the invention relates to a transgenic plant comprising the recombinant vector comprising a polynucleotide molecule comprising a sequence selected from the group consisting of: (a) a sequence encoding a polypeptide at least 85% identical to SEQ ID NO:2 or 4, wherein the polypeptide regulates plant leaf senescence; (b) a sequence comprising SEQ ID NO:1 or 3; (c) a sequence hybridizing to (b) under wash conditions of 0.15 M NaCl and 70° C. for 10 minutes, wherein the sequence encodes a protein that regulates plant leaf senescence; (d) a sequence comprising at least 85% sequence identity over the full length of the SEQ ID NO:1 or 3, wherein the sequence encodes a protein that regulates plant leaf senescence; and (e) a sequence complementary to (a), (b), (c) or (d); further in which the polynucleotide sequence is operably linked to a heterologous promoter functional in plants. In some embodiments the transgenic plant of may further be defined as a dicotyledonous plant. In particular embodiments the transgenic plant may further be defined as a poplar, a willow, a eucalyptus, a hemp, a Medicago sp., a Lotus sp., a Trifolium sp., a Melilotus sp., a Vinca sp., a Glycine sp., a Nicotiana sp., a Vitis sp., an Arabidopsis sp. or a Ricinus sp. In other embodiments the transgenic plant may further be defined as a monocotyledonous plant. In particular embodiments the transgenic plant may further defined be as a rice, a wheat, a barley, a maize, a switchgrass, an oat, a sugarcane, a rye or a sorghum. In certain embodiments the transgenic plant is further defined as an $R_0$ transgenic plant. In other embodiments the transgenic plant may further be defined as a progeny plant of any generation of an $R_0$ transgenic plant, wherein the transgenic plant has the nucleic acid molecule from the $R_0$ transgenic plant.

Another embodiment of the invention provides a seed of the transgenic plant, wherein the seed comprises the nucleic acid molecule. In certain embodiments, the invention relates to such a seed wherein nitrogen content is increased relative to that found in seed of an otherwise isogenic plant lacking the recombinant vector comprising a polynucleotide molecule comprising a sequence selected from the group consisting of: (a) a sequence encoding a polypeptide at least 85% identical to SEQ ID NO:2 or 4, wherein the polypeptide regulates plant leaf senescence; (b) a sequence comprising SEQ ID NO:1 or 3; (c) a sequence hybridizing to (b) under wash conditions of 0.15 M NaCl and 70° C. for 10 minutes, wherein the sequence encodes a protein that regulates plant leaf senescence; (d) a sequence comprising at least 85% sequence identity over the full length of the SEQ ID NO:1 or 3, wherein the sequence encodes a protein that regulates plant leaf senescence; and (e) a sequence complementary to (a), (b), (c) or (d); further in which the polynucleotide sequence is operably linked to a heterologous promoter functional in plants.

A host cell transformed with the recombinant vector is provided as another aspect of the invention. In one embodiment, the host cell is a plant cell.

The invention further provides a method of altering the distribution of one or more nutrient in a plant, the method comprising expressing in the plant a recombinant vector comprising a polynucleotide molecule comprising a sequence selected from the group consisting of: (a) a sequence encoding a polypeptide at least 85% identical to SEQ ID NO:2 or 4, wherein the polypeptide regulates plant leaf senescence; (b) a sequence comprising SEQ ID NO:1 or 3; (c) a sequence hybridizing to (b) under wash conditions of 0.15 M NaCl and 70° C. for 10 minutes, wherein the sequence encodes a protein that regulates plant leaf senescence; (d) a sequence comprising at least 85% sequence identity over the full length of the SEQ ID NO:1 or 3, wherein the sequence encodes a protein that regulates plant leaf senescence; and (e) a sequence complementary to (a), (b), (c) or (d); further in which the polynucleotide sequence is operably linked to a heterologous promoter functional in plants; further wherein expression of the nucleic acid molecule alters the distribution of one or more nutrient in the plant when compared to a plant of the same genotype that lacks the nucleic acid molecule. In some embodiments the nutrient is crude protein. In certain embodiment the plant is an $R_0$ transgenic plant. In other embodiments the plant is a progeny plant of any generation of an $R_0$ transgenic plant, wherein the transgenic plant has the nucleic acid molecule from the $R_0$ transgenic plant. A method wherein the altered distribution of one or more nutrient is a decrease of one or more nutrients in the leaves is another embodiment of the invention.

In yet other embodiments, such a method is contemplated wherein the plant has altered development or morphology when compared to a plant of the same genotype that lacks the nucleic acid molecule. In a particular embodiment, the altered development is altered leaf senescence.

In yet another aspect, the invention provides a method of producing plant biomass, the method comprising: (a) obtaining a plant comprising the recombinant vector described above; (b) growing the plant under plant growth conditions to produce plant tissue from the plant; and (c) preparing biomass from the plant tissue. In some embodiments the method comprises preparing biomass comprises harvesting the plant tissue. In further embodiments the biomass may be used for biofuel.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

(Senescence associated gene 12, At5g45890) after spraying of DMSO (1/1000) or estradiol (100 µM) for different time. The expression level of UBQ10 (At4g05320) was used as an internal control.

Figure 8:
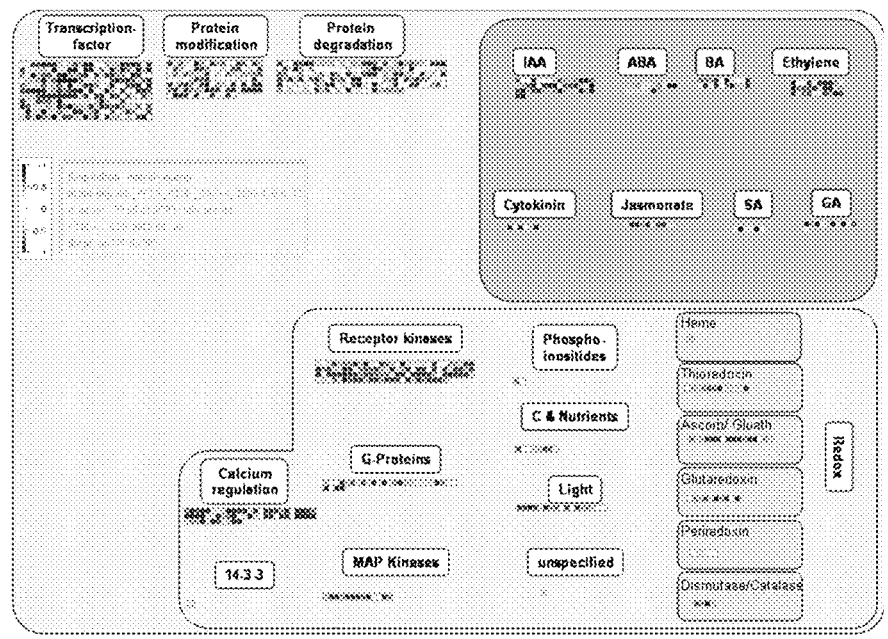
Figure 8:
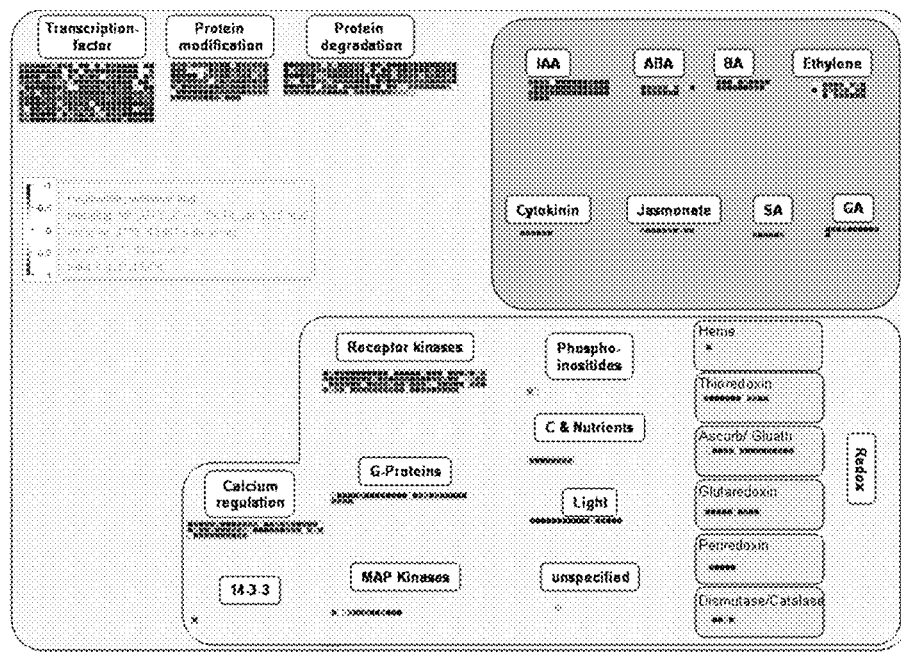

FIG. 8: Overview of regulatory network visualized by MapMan 3.5.1 software (Thimm et al., 2004). (a) 6 h after EST treatment, (b) 72 h after EST treatment.

Figure 9:
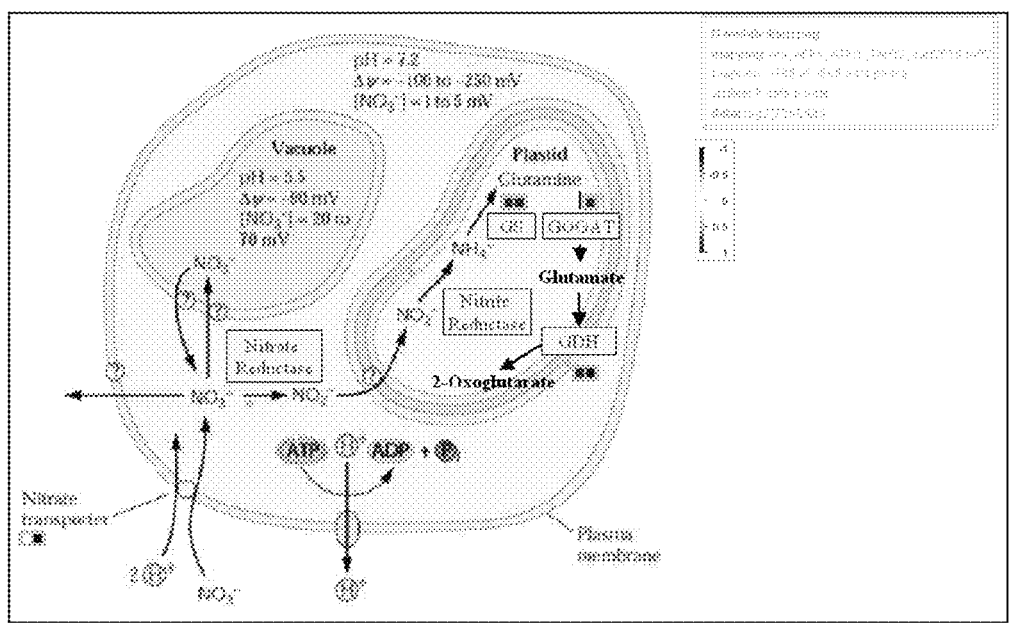

FIG. 9: Overview of nitrogen metabolism steps regulated by pvNAC-VS1. Genes involved in leaf nitrogen remobilization, GS[GLN1.1 (At5g37600), GLN1.3 (AT3g17820)], Fd-GOGAT (At2g41220) and GDH2 (At5g07440) were up-regulated while NTP2 (nitrate transporter, At2g26690) and GDH1 (At5g18170) were down-regulated.

DESCRIPTION OF SEQUENCE LISTING

Figure 2:
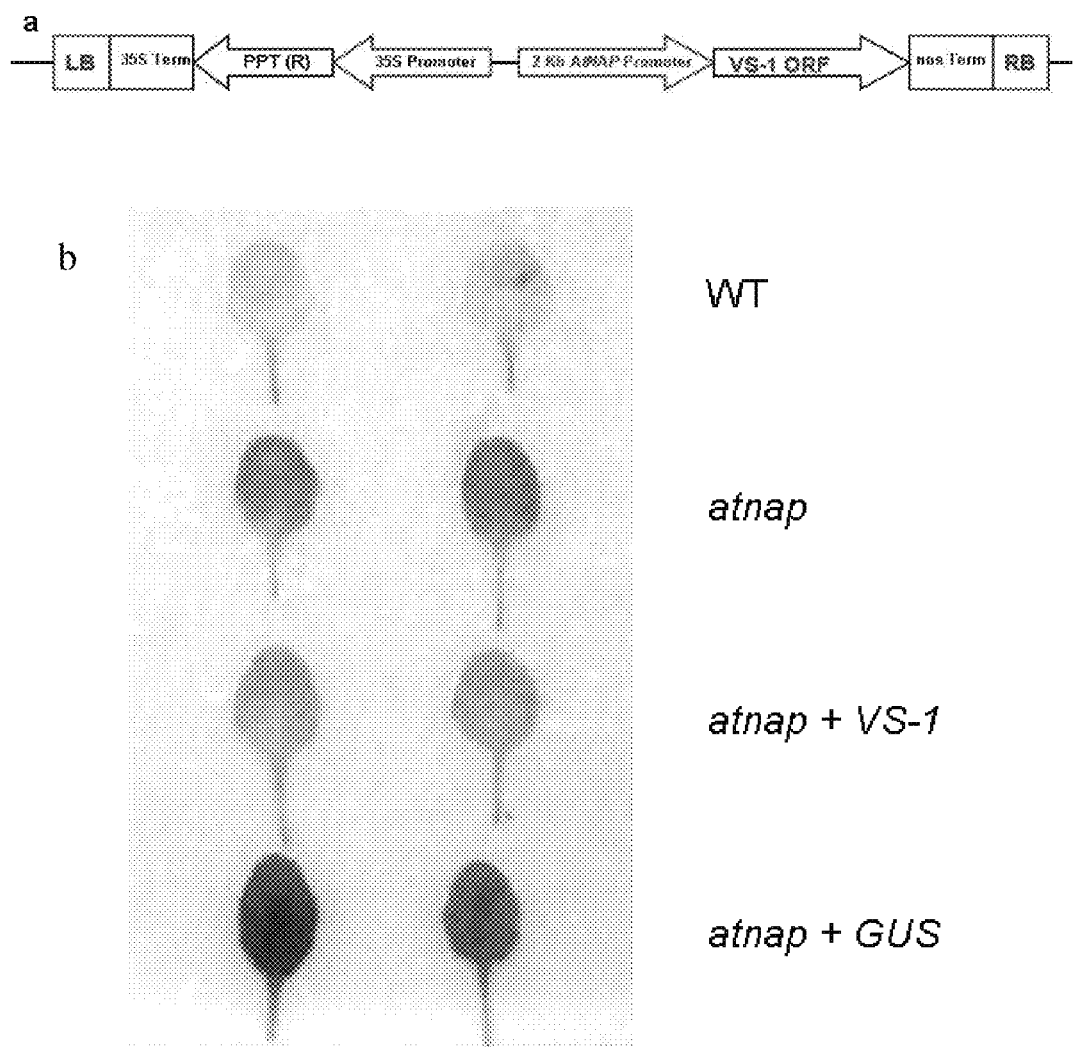
FIG. 2: Complementation of the null mutant of AtNAP via constitutive expression. (a) Structure of the T-DNA used for complementation by constitutive expression of AtNAP null mutant plants. The construct was built from pCAMBIA3301 (www.cambia.org; CSIRO, Canberra, AU). The *Panicum virgatum* VS-1 open reading frame was fused to a 2 kb promoter sequence from AtNAP ("pAtNAP::VS-1") and transformed into the AtNAP mutant. (b) Phenotypic comparisons of detached leaves from wild-type plants ("WT"); AtNAP null plants ("atnap"); AtNAP null mutant plants transformed with pAtNAP::VS-1 ("atnap+VS-1"); and a negative control ("atnap+GUS"). (c) Phenotype comparison and the chlorophyll contents of detached leaves of wildtype, atnap mutant and complementation transgenics in constitutive expression system. The leaves were incubated in full darkness for 5 days.
Figure 2:
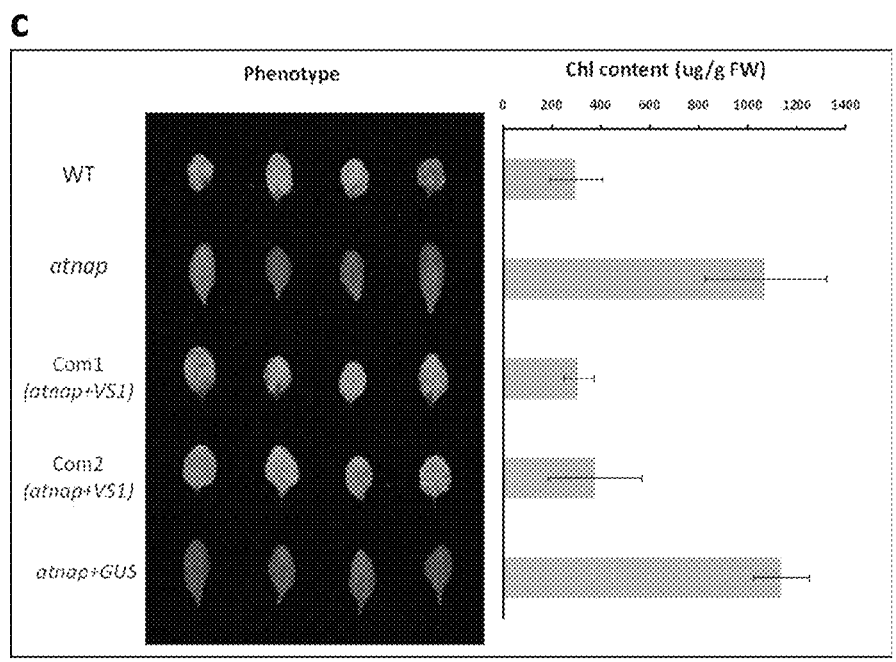

SEQ ID NO:1—cDNA sequence of *Panicum virgatum* VS-1
SEQ ID NO:2—protein sequence of *Panicum virgatum* VS-1
SEQ ID NO:3—cDNA sequence of *Panicum virgatum* AP-2
SEQ ID NO:4—protein sequence of *Panicum virgatum* AP-2
SEQ ID NO:5—cDNA sequence of *Arabidopsis thaliana* AtNAP
SEQ ID NO:6—protein sequence of *Arabidopsis thaliana* AtNAP
SEQ ID NO:7—sequence of *Arabidopsis thaliana* AtNAP promoter depicted in FIG. 2A
SEQ ID NOs:8-16—primer sequences as described in examples.
SEQ ID NOs:17-22—NAC TF peptide sequences aligned in FIG. 4B.

DETAILED DESCRIPTION OF THE INVENTION

The invention overcomes limitations of the prior art by providing plant genes (pvNAC-VS1 and AP-2) that affect leaf senescence. In certain embodiments, such sequences affect the timing of leaf senescence and/or protein content of seeds. Plants not expressing either pvNAC-VS1 or AP-2 may exhibit delayed or absent leaf senescence. The sequence of pvNAC-VS1 is provided herein as SEQ ID NO:1, with the encoded protein is provided as SEQ ID NO:2. AP-2 is provided herein as SEQ ID NO:3, with the encoded protein as SEQ ID NO:4. It is believed that AtNAP (SEQ ID NO:5 encoding SEQ ID NO:6) is an orthologue of either or both of pvNAC-VS1 or AP-2, by virtue of their very similar structure, and their similar functions demonstrated herein.

Further, the subcellular localization of pvNAC-VS1, which was found to localize to the nucleus, is consistent with its role as a transcriptional regulator. Induced expression of pvNAC-VS1 demonstrated that genes involved in senescence as well as nitrogen metabolism and mobilization were affected by pvNAC-VS1 expression. Results of constitutive expression of pvNAC-VS1 in transgenic *Arabidopsis* leaf and seed tissue demonstrated that over-expression of pvNAC-VS1 transcription factor in leaves of a transgenic plant results in increased protein content in seeds of the plant.

Thus, methods and compositions for enhancing the protein content of plant seeds are provided. Further, methods and compositions of regulating (e.g. hastening) senescence of plant vegetative tissues are also provided, which are of use for efficient production of biomass for biofuel.

I. NUCLEIC ACIDS, POLYPEPTIDES AND PLANT TRANSFORMATION CONSTRUCTS

Certain embodiments of the current invention concern polynucleotide sequences comprising a pvNAC-VS1 or AP-2 coding sequence. Exemplary coding sequences for use with the invention include SEQ ID NO:1 or 3 encoding the polypeptides of SEQ ID NO:2 or 4, respectively.

The invention provides a nucleic acid sequence identical over its entire length to each coding sequence provided herein. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The nucleic acid can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Nucleic acids of the present invention also include nucleic acids comprising a structural gene and the naturally associated sequences that control gene expression.

Another aspect of the present invention relates to the polypeptide sequences provided herein, as well as polypeptides and fragments thereof, particularly those polypeptides that exhibit VS-1/AP-2 activity and also those polypeptides that have at least 85% identity, more preferably at least 90% identity, and most preferably at least 95% identity to a polypeptide sequence selected from the group of sequences set forth herein, and also include portions of such polypeptides, wherein such portion of the polypeptide preferably includes at least 30 amino acids and more preferably includes at least 50 amino acids.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, S., et al., NCBI NLM NIH, Bethesda, Md. 20894; Altschul, S., et al., 1990). The well known Smith Waterman algorithm can also be used to determine identity.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

Figure 3:
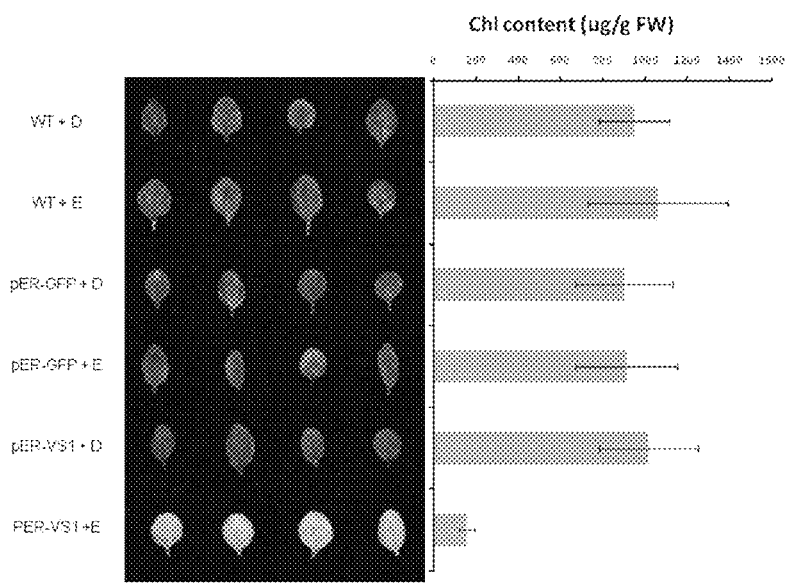
FIG. 3: Complementation of the null mutant of AtNAP via estradiol-inducible expression system. (a) Phenotype comparison and chlorophyll contents of detached leaves of wild-type and transgenic plants of pER-GFP and pER-VS1. The leaves were incubated on filter paper wetted by 1/1000 DMSO (D) or 100 uM estradiol ("EST") (E) under continuous light (120 μmol at 22° C.) for 5 days. (b) Typical phenotype and chlorophyll content of mature leaves from DMSO or EST sprayed pER-GFP and pER-VS1 plants. (c) Whole plant phenotype after spraying with DMSO (1/1000) or Estradiol (EST, 100 μM) solution and kept under continuous light. The arrows indicate areas of leaf yellowing in EST-sprayed transgenic plant. (d) induced expression of pvNAC-VS1 by EST in transgenic plants.
Figure 3:
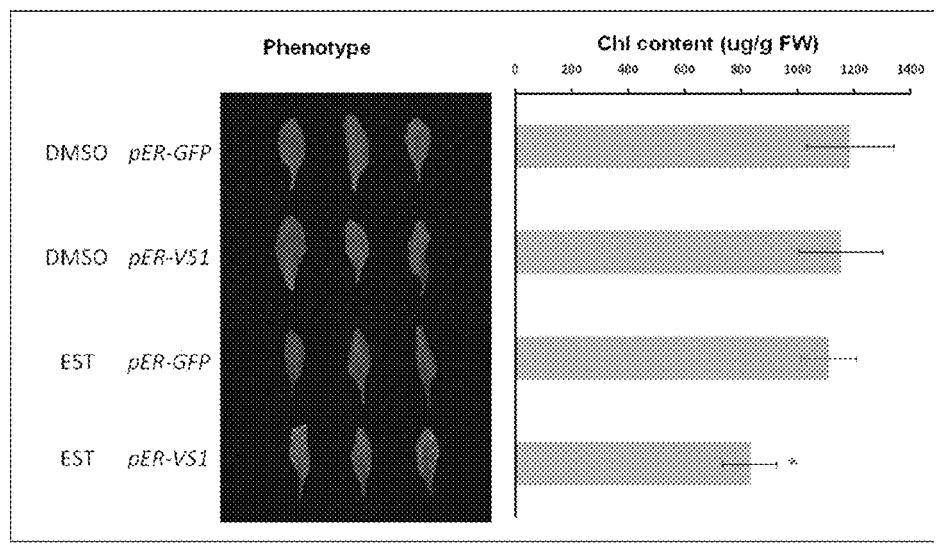
Figure 3:
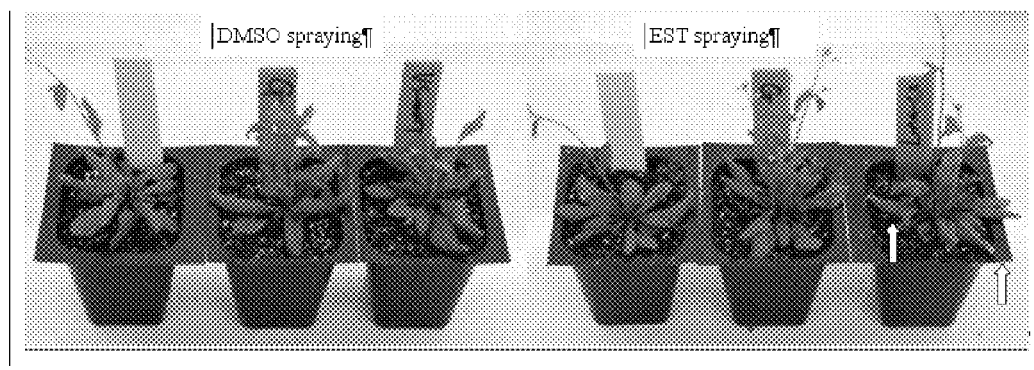
Figure 3:

It is further recognized that a polypeptide at least 85%, 90%, 92%, 95%, or 98% identical to SEQ ID NO:2 or 4 that is a VS-1 or AP-2 (i.e., modifies plant development or morphology, especially leaf senescence) could be readily identified as such by the skilled artisan by comparison of the polypeptide sequence with SEQ ID NO:2 or 4, since the sequences provided in the Examples establish regions having conserved or identical amino acid sequences, which would be expected to also be conserved in an orthologue to retain activity. Areas where amino acid residues are conserved or identical can be identified without undue experimentation in FIG. 3A, pointing out residues that are likely to be important for activity. Further, nucleic acid sequences encoding VS-1 or AP-2 can be identified without undue experimentation by determining the encoded amino acid sequence and comparing that amino acid sequence with the nine sequences provided in FIG. 3.

Provided herein are also nucleic acids capable of hybridizing to the nucleic acid sequences identified herein, for example, of SEQ ID NO:1 or 3. As used herein, "hybridization," "hybridizes" or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. In some embodiments, the sequence encodes a protein that modifies plant leaf senescence, as discussed above. Complements to any of the above-described nucleic acid sequences are also provided.

The nucleic acids provided herein can be from any source, e.g., identified as naturally occurring in a plant, or synthesized, e.g., by mutagenesis of known sequences SEQ ID NO:1 or 3, or sequences encoding SEQ ID NO:2 or 4. Where naturally occurring in a plant, the invention contemplates a naturally occurring sequence from any plant. In some embodiments, the plant is a dicotyledonous plant, for example a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or a *Glycine* sp. In other embodiments, the plant is a monocotyledonous plant, for example a rice, a wheat, a barley, a maize, a switchgrass, an oat, a sugarcane, a rye or a sorghum.

Coding sequences may be provided in a recombinant vector operably linked to a heterologous promoter functional in plants, in either sense or antisense orientation. Expression constructs are also provided comprising these sequences, including antisense oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

The choice of any additional elements used in conjunction with the VS-1 or AP-2 coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. In one embodiment of the invention, the CaMV 35S promoter is used to express VS-1 or AP-2 coding sequences.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that VS-1 or AP-2 coding sequences may be introduced under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

B. Terminators

Transformation constructs prepared in accordance with the invention will typically include a 3' end DNA sequence that acts as a signal to terminate transcription and allow for the polyadenylation of the mRNA produced by coding sequences operably linked to a promoter. In one embodiment of the invention, the native terminator of a VS-1 or AP-2 coding sequence is used. Alternatively, a heterologous 3' end may enhance the expression of sense or antisense VS-1 or AP-2 coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the invention will be in the alteration of plant phenotypes by genetic transformation with VS-1 or AP-2 coding sequences. The VS-1 or AP-2 coding sequence may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. GENETIC TRANSFORMATION

Additionally provided herein are transgenic plants transformed with the above-identified recombinant vector encoding an VS-1 or AP-2, or a sequence modulating expression thereof.

Suitable methods for transformation of plant or other cells for use with the current invention are believed to include virtually any method by which DNA can be introduced into a cell, such as by direct delivery of DNA such as by PEGmediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), maize (Ishidia et al., 1996) and switchgrass (*P. virgatum* L., Somleva et al., 2002).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present invention expressing heterologous VS-1 or AP-2 can be of any species. In some embodiments, the transgenic plant is a dicotyledonous plant, for example a plant used in biomass and forage crop production such as a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or a *Glycine* sp. In other embodiments, the plant is a monocotyledonous plant, for example a rice, a wheat, a barley, a maize, a switchgrass, an oat, a sugarcane, a rye or a sorghum. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the above-described transgenic plant are also contemplated, particularly where the seed comprises the nucleic acid sequence. Additionally contemplated are host cells transformed with the above-identified recombinant vector. In some embodiments, the host cell is a plant cell.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazzeri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

III. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. EVALUATION OF THE DISTRIBUTION OF NUTRIENTS

As previously discussed, modulation of the expression of VS-1 or AP-2 is expected to affect leaf senescence. Thus, a method of altering the distribution of one or more nutrients in a plant is provided. The method comprises expressing in the plant the above-identified recombinant vector comprising a VS-1 or AP-2 coding region, where the expression of the nucleic acid sequence alters the distribution of one or more nutrients in the plant when compared to a plant of the same genotype that lacks the nucleic acid sequence. In these embodiments, the plant can be the $R_0$ transgenic plant. Alternatively, the plant can be a progeny plant of any generation of an $R_0$ transgenic plant, where the transgenic plant has the nucleic acid sequence from the $R_0$ transgenic plant.

In some of these embodiments, the plant has altered development or morphology when compared to a plant of the same genotype that lacks the nucleic acid sequence. An example of altered development or morphology that can be observed in the plants of these methods is altered leaf senescence.

The plants with modulated expression of VS-1 or AP-2 can also be used to produce plant biomass, for example by obtaining the above-identified plant expressing a heterologous VS-1 or AP-2, growing said plant under plant growth conditions to produce plant tissue from the plant; and preparing biomass from said plant tissue. The biomass can be subsequently used for any purpose, for example to produce biofuel.

V. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected VS-1 or AP-2 coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:

(a) plant seeds of the first (starting line) and second (donor plant line that comprises a transgene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. DEFINITIONS

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Plant senescence: The process of aging in plant tissues. During senescence, metabolites from senescing tissues such as leaves may be remobilized to other parts of a plant, such as seeds, for use or storage. Hastening the senescence process may also allow for earlier harvest of biomass for biofuel.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Subcellular Localization of the VS-1 and AP-2 Proteins of *Panicum virgatum*

The present inventors have isolated two genes, VS-1 and AP-2 (SEQ ID NO:1 or SEQ ID NO:3), with homology to NAC family transcription factors from *Panicum virgatum* (switchgrass). These genes were identified by extracting total RNA from senescent leaves of switchgrass cultivar Summer VS16 or AP13 plants. Plants were propagated by asexual culture of nodal tissue and grown in the greenhouse at a temperature range of about 25-29° C., with a 16-h light period from 0600 to 2200 hours facilitated by supplementary lighting and with relative humidity around 50%. *Arabidopsis* ecotype Columbia-0 was used as wild type. A T-DNA insertion mutant atnap (At1g69490) (Guo & Gan, 2006) was obtained from the *Arabidopsis* Biological Resource Center (Ohio State University). The homozygous mutant was confirmed by PCR using genomic DNA prepared from wild-type or mutant plants as a template with two gene-specific primers, forward 5'-GAAATGAAACAAGATACACAAAGTCAC-3' (SEQ ID NO:8), and reverse 5'-AAGCTTCGGCCTAAGT-GTCAC-3' (SEQ ID NO:9), and a T-DNA left border primer 5'-ATTTTGCCGATTTCGGAAC-3' (SEQ ID NO:10).

Senescent leaves with yellowing tips of switchgrass VS16 plants were used for total RNA extraction using TRIZOL (Invitrogen, USA) according to the manufacturer's instructions. Purified RNA was treated with RNase-free DNase I (QIAGEN, Valencia, Calif., USA). First strand cDNA was synthesized by Superscript® III reverse transcriptase (Invitrogen, USA) with 2 µg purified total RNA as template. The cDNA was used as template to conduct 5' and 3'-RACE (Rapid Amplification of cDNA Ends) (FirstChoice® RLM-RACE Kit, Ambion, USA). The two inner primers for 5'-RACE were: 5'-ACTCGTGCATGATCCAGTYKGT-3' (SEQ ID NO:11) and 5'-KCGGGSWGAAGAAGTAC-CACTC-3' (SEQ ID NO:12). The 3'-RACE was conducted with two forward primers: 5'-TCGACCTCTACAAGTTC-GAYCC-3' (SEQ ID NO:13) and 5'-GCGAGMAGGAGTG-GTACTTCTT-3' (SEQ ID NO:14).

Full-length cDNAs were amplified, cloned, and sequenced from the VS16 and AP13 cDNA and the identified genes were named "pvNAC-VS1" or "VS-1," and AP-2, respectively. The deduced proteins, VS-1 and AP-2, contained conserved NAC domains in their N-terminal ends, identifying them as putative NAC family transcription factors.

Figure 1:
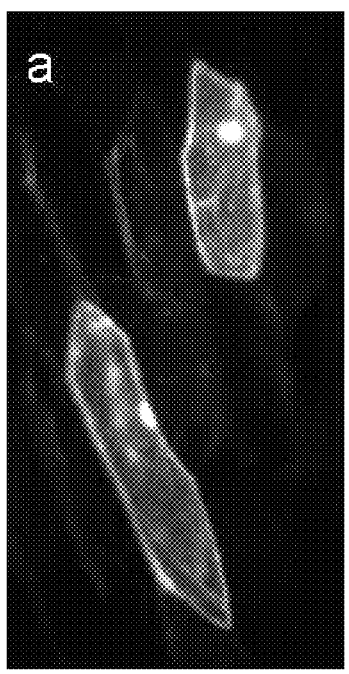
FIG. 1: Subcellular localization of VS-1:GFP translational fusion protein. (a) Transient GFP expression in onion epidermal cells transformed by particle bombardment with 35S: GFP as control. (b) Transient GFP expression in onion epidermal cells transformed by particle bombardment with 35S:: VS-1:GFP. (c) Structure of gene fusion construct of VS1-GFP in pAVA121 vector.
Figure 1:
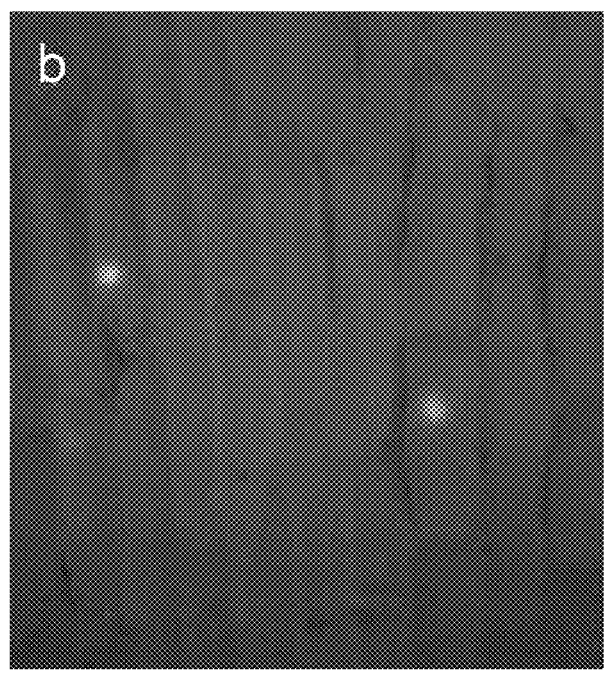
Figure 1:

To test the potential for the VS-1 and AP-2 proteins to act as transcriptional regulators, the subcellular localization of the proteins was examined. Translational fusions of VS-1: GFP were constructed, and placed under control of the constitutive 35S promoter (p35S::VS-1:GFP) (FIG. 1C). As a control, p35S::GFP constructs were also generated. The open reading frame of pvNAC-VS1 was cloned into pAVA121 vector (von Arnim et al., 1998).

pCAMBIA3301 vector containing a CaMV-35S driven GUS reporter was used as 35S-GUS. An approximately 2.0-kb AtNAP (At1g69490) promoter sequence ($P_{NAP}$) was amplified using primer pair G1807 and G1808 as described previously (Guo & Gan, 2006). After sequencing, the $P_{NAP}$ was fused via PstI and NcoI into 35S-GUS to replace the CaMV-35S promoter.

The open reading frame (ORF) of pvNAC-VS1 was amplified by PCR using a pair of specific primers: 5'-TTAGATC-TATGGCGGTAAGCTCTGC-3' (SEQ ID NO:15; forward primer; the underlined section is an engineered BglII site) and 5'-TAGGTCACCCTAGT-GTTTTTTTCTTTCATATTTGAATTTG-3' (SEQ ID NO:16; reverse primer; the underlined section is an engineered BstEII site). The pvNAC-vs-1 ORF was cloned into the $P_{NAP}$-GUS construct or into pCAMBIA3301 via BglII and BstEII sites to replace GUS sequences respectively. Each construct was transformed into onion epidermal cells by particle bombardment, for transient expression.

Subcellular localization of the GFP signal was examined by fluorescence microscopy using a confocal laser scanning microscope (TCS SP2 AOBS; Leica). In cells expressing the VS-1:GFP fusion protein, GFP was detected only in nuclei (FIG. 1B). In cells expressing free GFP, green fluorescence was detected in all cellular compartments of transformed cells, including in nuclei, at the plasma membrane, and in the cytoplasm (FIG. 1A). Similar results were obtained with the AP-2:GFP fusion protein. These results demonstrate that the VS-1 and AP-2 proteins are localized in the nucleus, consistent with their hypothesized roles as transcriptional regulators.

Example 2

Effect on Leaf Phenotype of AtNAP Null Plants by Constitutive Expression of pvNAC-VS1

Figure 4:
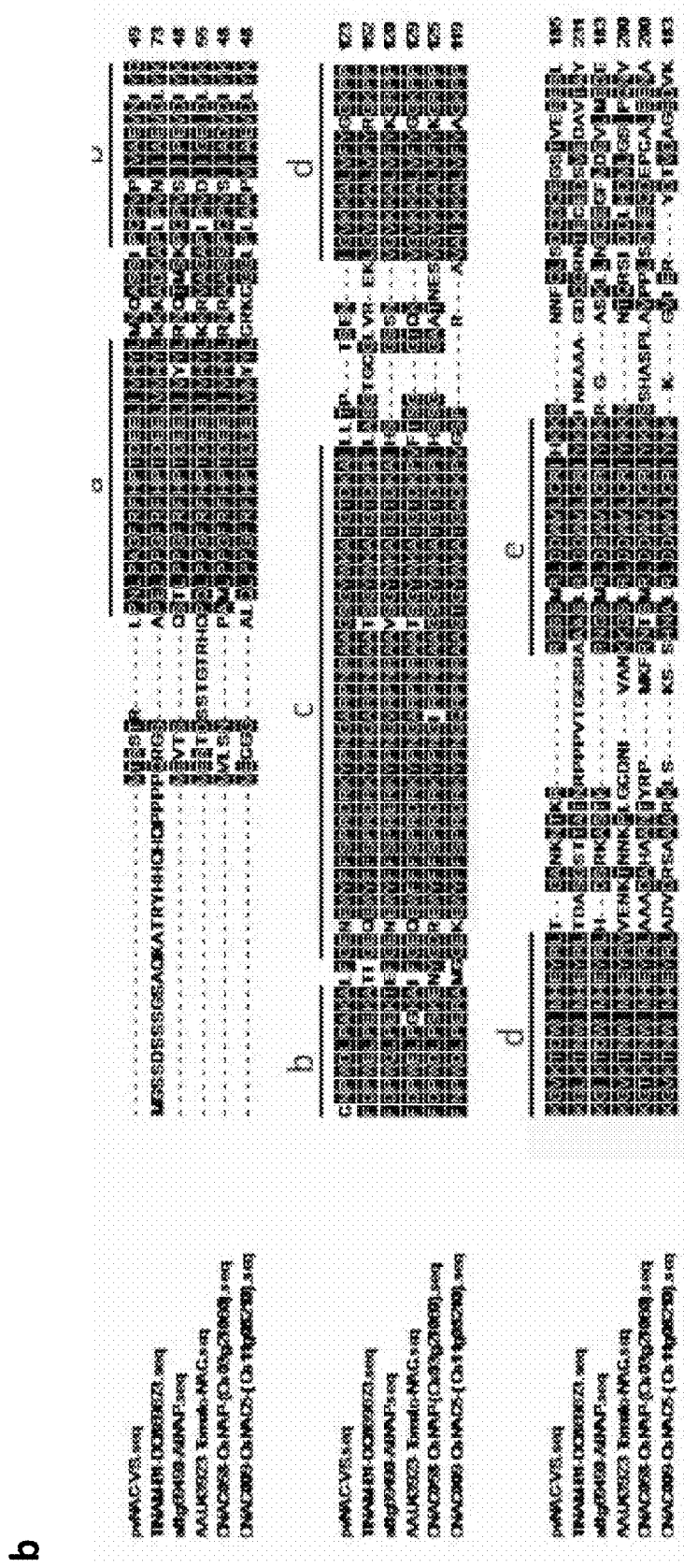
FIG. 4: (a) Sequence alignment of VS-1, AP-2 and AtNAP. (b) Alignment of pvNAC-VS1 encoded protein and several typical NAC TFs with known or supposed function in senescence and or nutrient remobilization. The letters a-b-c-d-e in the figure indicate the five motifs of N-terminal conserved domain in typical NAC TFs (c) Phylogeny of switchgrass VS-1 and representative NACs from rice as well as other known or putative NACs. Phylogenetic tree of pvNAC-VS1 protein and representative NAC TFs from rice and other plants with known or indicative functions. The branch encircled by dashed line was the subfamily containing pvNAC-VS1 (indicated by blue arrow) and NAC TFs either related to senescence in *Arabidopsis* (AtNAP) (Thimm et al., 2004) or nutrient remobilization in wheat (TtNAM-B1) (Sperotto, 2009) and rice (underlined by blue lines). The phylogenetic tree was produced by DNASTAR MegAlign software.
Figure 4:
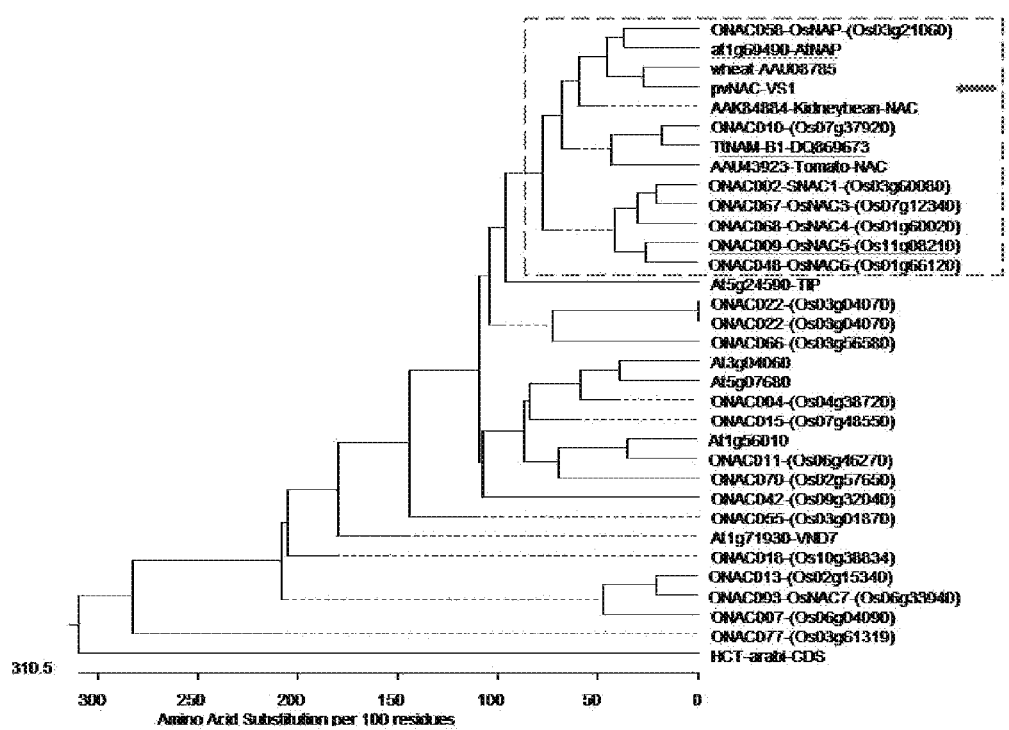

AtNAP has recently been demonstrated to play a key role in regulating leaf senescence in the model plant *Arabidopsis thaliana* (Guo and Gan, 2006), and AtNAP mutants exhibit a stay-green phenotype. cDNAs obtained by RACE were sequenced and putative NAC sequences were used for alignment and phylogenetic analysis. The Clustal W method of MegAlign (DNASTAR, Madison, USA) was used to perform alignment of deduced protein sequence of the putative switchgrass NAC with other NAC proteins. The phylogenetic tree was displayed by aligning rice representative NAC genes and NAC genes from other plants. This phylogenetic analysis with putative or confirmed NAC-like transcription factor function sequences demonstrated that the VS-1 protein of *Panicum virgatum* is closely related to AtNAP (FIG. 4B). The branch of the phylogenetic tree encircled by dashed line includes the subfamily containing VS-1 (indicated by an arrow in FIG. 4C) and NAC TFs related to senescence in *Arabidopsis* (AtNAP) and nutrient remobilization in wheat (NAM-A1 and B1) (underlined in FIG. 4C).

To test whether the VS-1 and AP-2 proteins are able to functionally complement phenotypes related to loss of AtNAP, a complementation construct was created in which a 2 kb AtNAP promoter sequence (SEQ ID NO:7) directed expression of the open reading frame of VS-1 (pAtNAP::VS-1; FIG. 2A).

The pAtNAP::VS-1 construct was transformed by *Agrobacterium* C58 into plants with a null mutation in AtNAP via floral dip (Clough & Bent, 1998). T2 and T3 homozygous transgenic plants were used for phenotypic comparisons. Fully expanded, non-senescing leaves were detached from wild-type ("WT"), AtNAP null ("atnap"), AtNAP null transformed with pAtNAP::VS-1 ("atnap+VS-1"), or AtNAP null transformed with pAtNAP::GUS ("atnap+GUS") plants and incubated on wet filter paper in total darkness at 22° C. for seven days. As shown in FIG. 2B, leaves from wild-type plants began to senesce during this period, and turned yellow due to loss of chlorophyll. Leaves from atnap plants remained green, indicating no loss of chlorophyll and therefore no senescence. Leaves of atnap plants transformed with pAtNAP::VS-1 plants turned yellow and senesced, similar to wild-type, i.e., the mutant's stay-green phenotype was suppressed. The leaves of atnap mutant plants transformed with AtNAP+GUS remained green like untransformed atnap leaves. Visual analyses were confirmed by chlorophyll measurement (FIG. 2C).

Example 3

Complementation of AtNAP Null Plants by an Inducible Expression System

An estradiol-inducible expression system was used to study effects of pvNAC-VS1 expression. The pvNAC- VS10RF was cloned via AscI and SpeI sites into an estradiol-inducible vector pER8 (Zuo et al. 2000) and named pER-VS1. The pER8 vector containing GFP as reporter gene (pER-GFP) was used as an "empty vector control." Constructs were transferred respectively into *Agrobacterium tumefaciens* strain C58 by the freeze-thaw method (Chen & Sherwood, 1994).

Following floral dip transformation of *Arabidopsis* (Clough & Bent, 1998) with pER8-GFP or pER8—VS1 for inducible over expression, transgenic plants were selected by sowing seeds on ½ strength MS agar plates with hygromycin (15 mg/L). Homozygous $T_3$ plants were used for further analysis.

For detached leaf tests, leaves number 5 or 6 from 3-week-old plants of transgenic and non-transformed *Arabidopsis* were excised and placed on filter paper moistened with $ddH_2O$ in a Petri dish with adaxial side facing up. The plates were kept in darkness at 22° C. for 5-7 days. Estrogen treatments were conducted as previously described (Zuo et al., 2000). Detached leaves from *Arabidopsis* plants with the EST-inducible pvNAC-VS1 construct, and wild type controls, were placed on filter paper moistened with 100 μm estradiol (EST) or DMSO solution in Petri dishes with adaxial side facing up. The plates were kept under 120 μmol white light at 22° C. for 5-7 days. For intact plant tests, three-week-old plants were sprayed with 100 μm estradiol (EST) or DMSO solution to ensure total coverage of the foliage area. The sprayed plants were incubated under plastid dome for 24 hours and kept under continuous white light. The phenotype of plants was observed, and leaves were harvested for physiological and molecular analysis.

It was found that expression of pvNAC-VS1 was sufficient to induce plant senescence as indicated by leaf yellowing in detached leaves and intact plants, also as seen by measuring chlorophyll content of the plant tissues (FIGS. 3A, 3B). Whole plant phenotype is shown in FIG. 3C. Arrows indicate areas of leaf yellowing after spraying transgenic plants with EST. The level of pvNAC-VS1 mRNA and specificity of estradiol-inducible pvNAC-VS1 expression in transgenic plants was also examined, with 18S ribosomal message as an internal control (FIG. 3D).

Example 4

Expression of pvNAC-VS1 in Switchgrass

Expression of pvNAC-VS1 in switchgrass leaves was studied during plant development. Switchgrass tillers at stages of vegetative-3, elongation-5, and reproductive-4, according to a quantification system for perennial grasses (Moore et al., 1991), were referred as young, medium and old tiller respectively. The expression level of pvNAC-VS1 was analyzed by quantitative RT-PCR in the first leaves (numbered from bottom to top) on different tillers and in leaves at different positions (top, intermediate and bottom) on old tillers. Leaves detached from tillers were incubated on wet filter paper in continuous darkness to artificially induce senescence.

Figure 5:
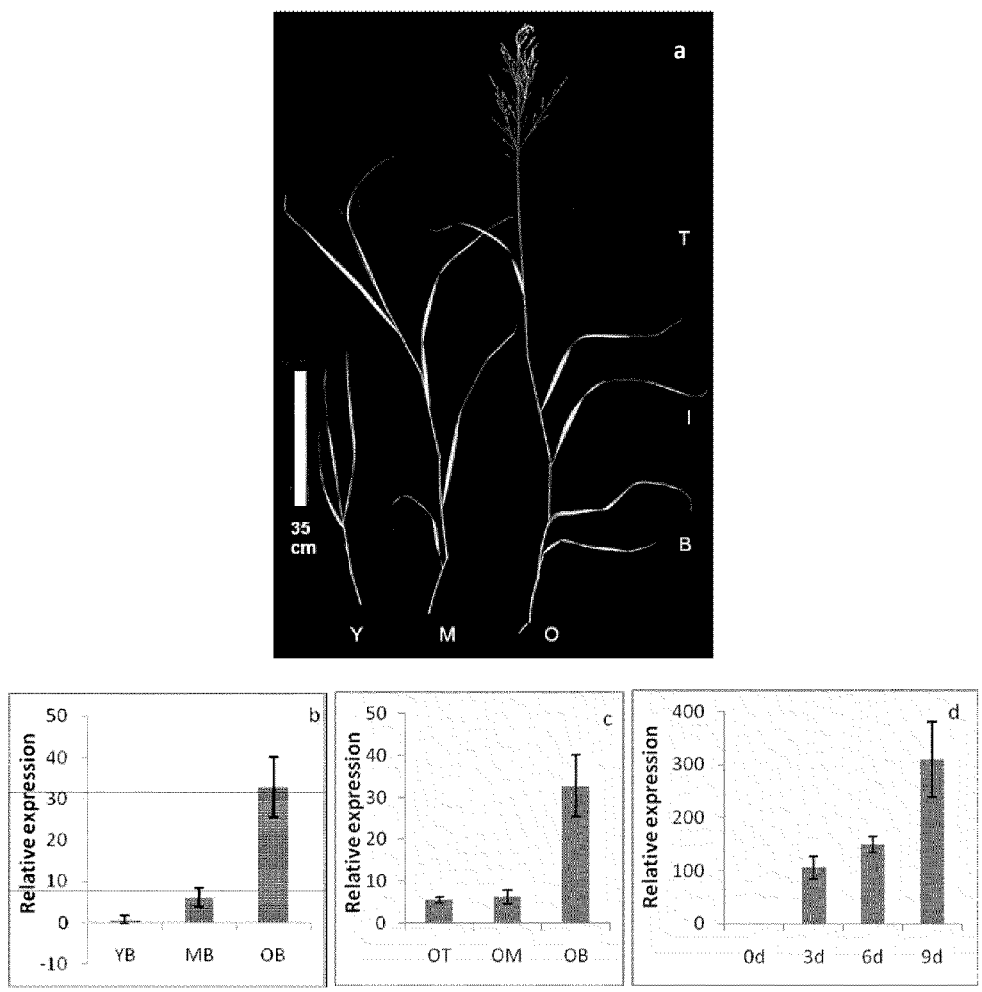
FIG. 5: (a) Phenotype of switchgrass young (Y), medium (M) and old (O) tillers and leaves at different position on tillers (T, top; I, intermediate and B, bottom). (b) the expression levels of pvNAC-VS1 in bottom leaves on young, medium and old tillers (YB, MB and OB). (c) the expression levels of pvNAC-VS1 in top, intermediate and bottom leaves on old tillers (OT, OI and OB). (d) the expression levels of pvNAC-VS1 in intermediate leaves which were detached from medium tillers and incubated on wet paper towel under continuous darkness for 0, 3, 6 and 9 days respectively.

The expression level of pvNAC-VS1 was measured by real-time PCR. Each 10-μL reaction included 2 μL primers (0.5 μM each primer), 5 μL Power Sybr (Applied Biosystems), 2 μL 1:10 diluted cDNA from the reverse transcription step, and 1 μL water. qRT-PCR data were analyzed using SDS 2.2.1 software (Applied Biosystems). Transcript levels were presented as normalized linearized values using the $2^{-\Delta\Delta C_T}$ method, where $C_T$ is the threshold cycle and UBQ10 was used as the internal control. pvNAC-VS1 expression increased significantly during senescence and in response to dark treatment. FIG. 5a shows the phenotype of young ("Y"), medium ("M"), and old ("O") tillers and leaves at different positions in the plant. FIG. 5B-C shows relative expression levels of pvNAC-VS1 in bottom leaves, and in top, intermediate, or bottom leaves on old tillers. FIG. 5D shows relative expression of pvNAC-VS1 in intermediate leaves which were detached from medium aged tillers and incubated on a wet paper towel under continuous darkness for 0, 3, 6, and 9 days, respectively. The results demonstrate that PVNAC-VS1 expression is consistent with its apparent role in regulating leaf senescence and nutrient remobilization in switchgrass.

Example 5

Effect of Constitutive Expression of pvNAC-VS1 TF in *Arabidopsis* Seeds

To examine whether pvNAC-VS1 expression could promote nitrogen remobilization to seeds, the pvNAC-VS1 transcription factor was constitutively expressed in wild type *Arabidopsis*. Twelve 35S-VS1 transgenic lines were selected for seed production, along with two empty-vector control transgenic lines (35S-GUS, "EVCK"). Seeds produced by 35S-VS1 constitutive over-expression lines or 35S-GUS transgenic plants were dried at 37° C. for at least three days, then ground into a fine powder using a SPEX SamplePrep 6870 Freezer/Mill (Metuchen, N.J., USA). The total nitrogen content (%) of each sample powder was analyzed by Ward Laboratories, Inc. (Kearney, Nebr., USA) using a combustion method (Horneck & Miller, 1998). Crude protein content may thus also be determined from total N content, as is known in the art (e.g. by Kjeldahl method and EU Scientific Committee for Foodstuffs recommendations of May 2003).

Figure 6:
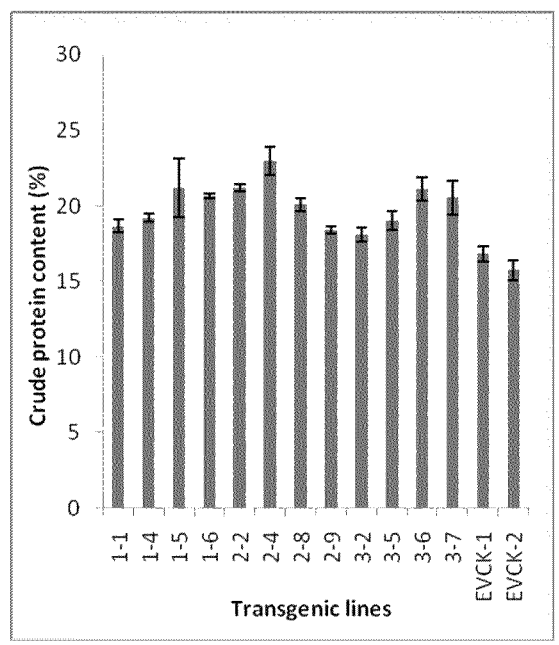
FIG. 6: (a) Crude protein content (%) in seeds of pvNAC-VS1 transgenic *Arabidopsis* lines and two empty vector control (EVCK). Error bars indicate standard deviation (n=3). (b) The positive relationship between crude protein content of seeds and the relative expression level pvNAC-VS1. Each point in figure represents an independent transgenic line.
Figure 6:
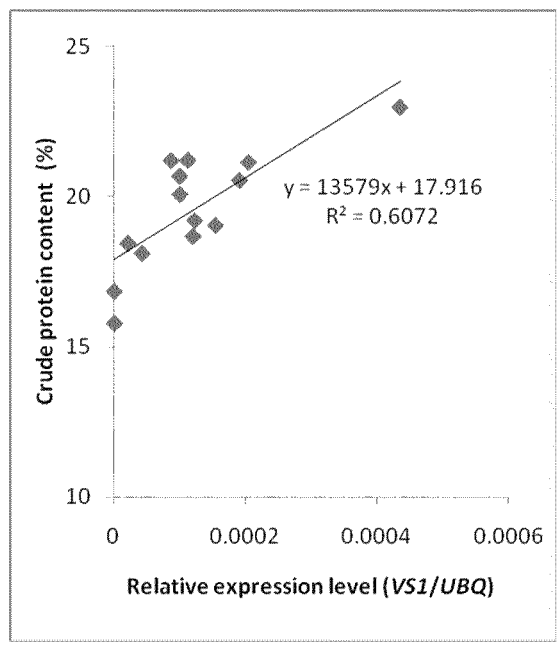

All 35S-VS1 transgenic seeds were shown to have a higher content of crude protein than EVCK lines (FIG. 6A), and a positive linear trend was found between crude protein content in seeds and pvNAC-VS1 expression levels (FIG. 6B). Therefore, pvNAC-VS1 over expression promoted nitrogen remobilization to *Arabidopsis* seeds, resulting in improved nutrient value.

Example 6

Transcriptome Analysis in *Arabidopsis*

Figure 7:
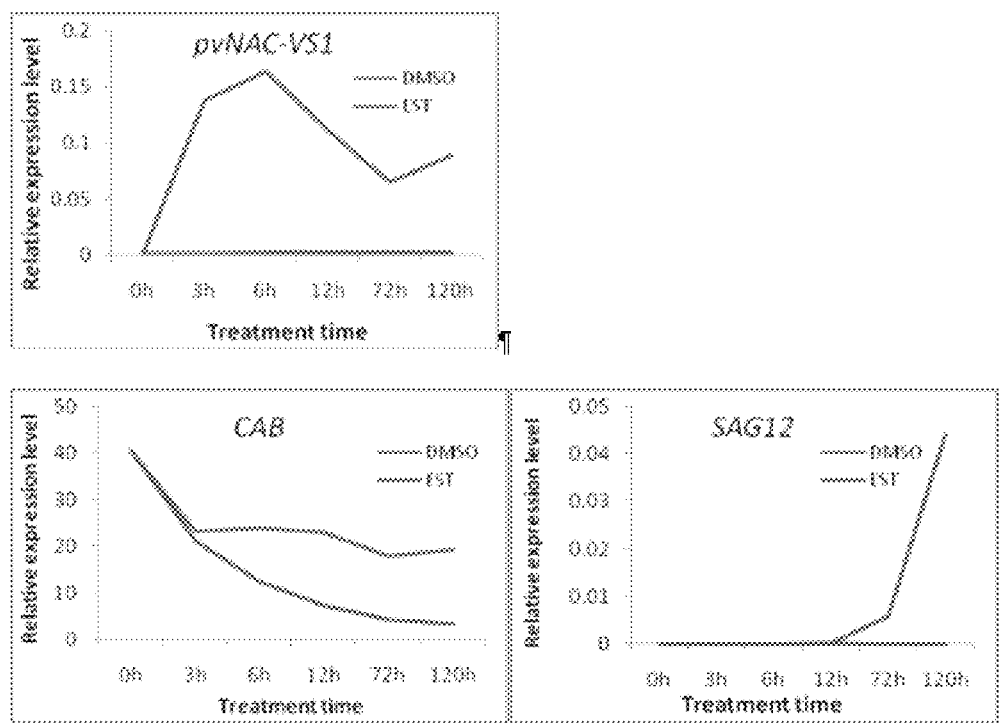
FIG. 7: Relative expression level of pvNAC-VS1, CAB (Chlorophyll a/b binding protein, At1g29930) and SAG12

The downstream regulatory network of pvNAC-VS1 was examined by transcriptome analysis of transgenic *Arabidopsis* leaves following estradiol-induced pvNAC-VS1 expression at 3 h, 6 h, 12 h, 72 h and 120 h (FIG. 7), to identify early and late responsive genes affected by pvNAC-VS1 expression.

The expression level of pvNAC-VS1 in estradiol-sprayed plants was determined by quantitative real-time PCR (qRT-PCR), as described above for qRT-PCR in Example 4. Total RNA samples from estradiol-treated leaves containing pER-VS1 were subjected to Affymetrix microarray analysis. RNA prepared from DMSO-sprayed pER-VS1 leaves and estradiol-sprayed pER-GFP leaves were used as the control lines to exclude genes which may respond to treatment of DMSO or estradiol. RNA was isolated with TRI-reagent according to the manufacturer's protocol (Invitrogen), cleaned, and concentrated using the RNeasy MinElute Cleanup Kit (Qiagen). 10 μg of purified RNA of three biological replicates were used for microarray analysis. Probe labeling, hybridization, and scanning were conducted according to the manufacturer's instructions (Affymetrix). Data normalization was conducted using robust multichip average (RMA). The presence/absence call for each probe set was obtained from DNAchip analyzer (dCHIP). Genes significantly expressed between the control and mutants were selected using associative analysis as described. Type I family-wise error rate was reduced by using a Bonferroni corrected P value threshold of 0.05/N, where N represents the number of genes present on the chip. The false discovery rate was monitored and controlled by Q value (falsediscovery rate) calculated using extraction of differential gene expression (EDGE; www.genomine.org/edge/; Leek et al., 2006).

Spraying of DMSO (1/1000) or estradiol (100 μM) was started at indicated times. The expression level of UBQ10 (At4g05320) was used as an internal control. In transgenic lines when comparing estradiol (EST) treatment with DMSO-only negative control, EST treatment led to increased expression of pvNAC-VS1 at about 3-6 hours following EST treatment, and also led to increasing expression of SAG12 (At5g45890; senescence associated gene) by 72-120 hours after EST treatment, while expression of CAB (At1g29930) declined relative to the control. Processes up-regulated by pvNAC-VS1 expression included regulation of transcription, protein modification and protein degradation (FIGS. 8A-8B) and nitrogen remobilization. The latter includes genes encoding two glutamine synthetases (GLN1.1 and GLN1.3), three GAD (GAD1, 3 and 4), glutamate dehydrogenase, GDH2, and glutamate oxoglutarate amino transferase, Fd-GOGAT. Genes for a nitrate transporter, NTP2 (nitrate transporter, At2g26690), and GDH1 (At5g18170) were down-regulated. Genes involved in leaf nitrogen remobilization, GS[GLN1.1 (At5g37600), GLN1.3 (AT3g17820)], Fd-GOGAT (At2g41220), and GDH2 (At5g07440) were up-regulated (FIG. 9).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042
Abdullah et al., *Biotechnology*, 4:1087, 1986.
Altschul et al., *J. Mol. Biol.*, 215:403-410, 1990.
Barton and Poethig, Development 119: 823-831, 1993.
Bates, *Mol. Biotechnol.* 2(2):135-145, 1994.
Battraw and Hall, *Theor. App. Genet.* 82(2):161-168, 1991.
Bendtsen et al., *J. Mol. Biol.* 340:783-795, 2004.
Bevan et al., *Nucleic Acids Research* 11(2):369-385, 1983.
Bhattacharjee et al., *J. Plant Bioch. Biotech.* 6, (2):69-73. 1997.
Biocomputing: Informatics and Genome Projects, Smith (Ed.), Academic Press, NY, 1993.
Birren, et al., *Genome Analysis* 1:543-559, 1997.
BLAST Manual, Altschul et al. (Eds.), NCBI NLM NIH, Bethesda, Md. 20894
Bower et al., *Plant J.* 2:409-416. 1992.
Buising and Benbow, *Mol Gen Genet.* 243(1):71-81. 1994.
Byrne, M. E., *PLoS Genet.* 2: e89, 2006.
Callis et al., *Genes Dev.* 1:1183-1200, 1987.
Carillo and Lipman, *SIAM J. Applied Math* 48:1073, 1988.
Casa et al., *Proc. Natl. Acad. Sci. USA* 90(23):11212-11216, 1993.
Chandler et al., *Plant Cell* 1:1175-1183, 1989.
Chen & Sherwood, *Biotechniques* 16:664-670, 1994.
Chiu et al., *Curr. Biol.* 6:325-330, 1996.
Chu et al., *Scientia Sinica* 18:659-668, 1975.
Chuck et al., *Plant Cell* 8:1277-1289, 1996.
Clark et al., *Cell* 89: 575-585, 1997.
Clough and Bent, *Plant J.* 16:735-743, 1998.
Computational Molecular Biology, Lesk (Ed.), Oxford University Press, NY, 1988.
Computer Analysis of Sequence Data, Part I, Griffin and Griffin (Eds.), Humana Press, NJ, 1994.
Conkling et al., *Plant Physiol.* 93:1203-1211, 1990.
Coulson, *Trends Biotech.* 12:76-80, 1994.
DE 3642 829
De Block et al., *EMBO J.* 6(9):2513-2518, 1987.
De Block et al., *Plant Physiol.* 91:694-701, 1989.
Dellaporta et al., In: *Chromosome Structure and Function: Impact of New Concepts,* 18th Stadler Genetics Symposium, 11:263-282, 1988.
Devereux et al., *Nucleic Acids Res.* 12(1):387, 1984.
Doerner, *Current Biology* 13: R368—R374, 2003.
Downward, *BMJ* 328(7450):1245-1248, 2004.
Ebert et al., *Proc. Natl. Acad. Sci. USA* 84:5745-5749, 1987.
Emanuelsson et al., *J. Mol. Biol.* 300:1005-1016, 2000.
Emery et al., *Curr Biol* 13: 1768-1774, 2003.
EPA App. 154,204
Eshed et al., *Curr Biol* 11: 1251-1260, 2001.
Eshed et al., *Development* 131: 2997-3006, 2004.
Fire et al., *Nature* 391(6669):806-811, 1998.
Fletcher et al., *Science* 283: 1911-1914, 1999.
Fraley et al., *Bio/Technology* 3:629-635, 1985.
Fromm et al., *Nature* 319:791-793, 1986.
Gallie et al., *Plant Cell* 1:301-311, 1989.
Gan and Amasino, *Plant Physiol.,* 113:313-319, 1997.
Gaston et al., *J. Environ. Qual.* 32:1422-1429, 2003.
Gelvin et al., In: *Plant Molecular Biology Manual,* 1990.
Ghosh-Biswas et al., *J. Biotechnol.* 32(1):1-10, 1994.
Guo & Gan, *Plant J.* 46:601-612, 2006.
Haecker et al., *Development* 131: 657-668, 2004.
Hagio et al., *Plant Cell Rep.* 10(5):260-264, 1991.
Haseloff et al., *Proc. Natl. Acad. Sci. USA* 94(6):2122-2127, 1997.
He et al., *Plant Cell Reports* 14 (2-3):192-196, 1994.
Hensgens et al., *Plant Mol. Biol.* 22(6):1101-1127, 1993.
Hentikoff and Hentikoff, *Proc. Natl. Acad. Sci. USA* 89:10915-10919, 1992.
Hiei et al., *Plant Mol. Biol.* 35(1-2):205-218, 1997.
Hinchee et al., *BioTechnol.* 6:915-922, 1988.
D. A. Horneck, R. O. Miller, In: Y. P. Kalra (ed)., *Handbook of Reference Methods for Plant Analysis.* CRC Press. Boca Raton, pp 75-83, 1998.
Hudspeth and Grula, *Plant Mol. Biol.* 12:579-589, 1989.

Ikuta et al., *BioTechnol.* 8:241-242, 1990.
Ishida et al., *Nat. Biotechnol.* 14(6):745-750, 1996.
Iwakawa et al., *Plant Cell Physiol.* 43: 467-478, 2002.
Jeong et al., *Plant Cell* 11: 1925-1934, 1999.
Kaeppler et al., *Plant Cell Reports* 9:415-418, 1990.
Kaeppler et al., *Theor. Appl. Genet.* 84(5-6):560-566, 1992.
Katz et al., *J. Gen. Microbiol.* 129:2703-2714, 1983.
Klee et al., *BioTechnology* 3(7):637-642, 1985.
Knittel et al., *Plant Cell Reports* 14(2-3):81-86, 1994.
Laux et al., *Development* 122: 87-96, 1996.
Lawton et al., *Plant Mol. Biol.* 9:315-324, 1987.
Lazzeri, *Methods Mol. Biol.* 49:95-106, 1995.
Leek et al., *Bioinformatics* 22:507-508, 2006.
Lehner et al., *Brief Funct. Genomic Proteomic.* 3(1):68-83, 2004.
Lin et al., *Plant Cell* 15: 2241-2252, 2003.
Liu et al., *Mol. Plant. Microbe Interact.* 11(1):14-22, 1998.
Long et al., *Nature* 379: 66-69, 1996.
Mallory et al., *EMBO J.* 23: 3356-3364, 2004.
Matsumoto and Okada, *Genes Dev.* 15: 3355-3364, 2001.
Mayer et al., *Cell* 95: 805-815, 1998.
McCabe and Martinell, *BioTechnology* 11(5):596-598, 1993.
McConnell et al., *Nature* 411: 709-713, 2001.
McCormac et al., *Euphytica* 99(1):17-25, 1998.
McHale and Koning, *Plant Cell* 16: 1730-1740, 2004.
McHale and Marcotrigiano, *Development* 125: 4235-4243, 1998.
McHale, *Planta* 186: 355-360, 1992.
Mihaliak et al., *Meth. Plant Biochem.* 9:261-279, 1993.
Moore et al., *Agron J.* 83:1073, 1991.
Murakami et al., *Mol. Gen. Genet.* 205:42-50, 1986.
Murashige and Skoog, *Physiol. Plant.* 15:473-497, 1962.
Murphy and Riley, *Anal. Chim. Acta* 27:31-36, 1962.
Nagatani et al., *Biotech. Tech.* 11(7):471-473, 1997.
Nardmann et al., 131: 2827-2839, 2004.
Needleman and Wunsch, *J. Mol. Biol.* 48:443-453, 1970.
Nielsen et al., *Protein Eng.* 10:1-6, 1997.
Nielsen, *Nat. Biotechnol.* 21(3):227-228, 2003.
Odell et al., *Nature* 313:810-812, 1985.
Ogawa et al., *Sci. Rep.* 13:42-48, 1973.
Olah and Sherwood, *Phytopathology* 61:65-69, 1971.
Omirulleh et al., *Plant Mol. Biol.* 21(3):415-428, 1993.
Otsuga et al., *Plant J* 25: 223-236, 2001.
Ow et al., *Science* 234:856-859, 1986.
PCT Appln. WO 92/17598
PCT Appln. WO 94/09699
PCT Appln. WO 95/06128
PCT Appln. WO 97/04103
PCT Appln. WO 97/41228
Pote et al., *J. Environ. Qual.* 32:2392-2398, 2003.
Potrykus et al., *Mol. Gen. Genet.* 199:183-188, 1985.
Prasher et al., *Biochem. Biophys. Res. Commun.* 126(3): 1259-1268, 1985.
Reichel et al., *Proc. Natl. Acad. Sci. USA,* 93(12):5888-5893, 1996.
Ritala et al., *Plant Mol. Biol.* 24(2):317-325, 1994.
Rogers et al., *Methods Enzymol.* 153:253-277, 1987.
Rommens et al., *Plant Physiol.* 135:421-431, 2004.
Sambrook et al., In: *Molecular cloning: a laboratory manual*, $2^{nd}$ Ed., Cold Spring Harbor Laboratory, NY, 1989.
Schumacher et al., *Plant Cell Rep.* 6:410-413, 1987.
Sequence Analysis in Molecular Biology, von Heinje (Ed.), Academic Press, NY, 1987.
Sequence Analysis Primer, Gribskov and Devereux (Eds.), Stockton Press, NY, 1991.
Sheen et al., *Plant J.* 8(5):777-784, 1995.
Singsit et al., *Transgenic Res.* 6(2):169-176, 1997.
Somleva et al., *Crop Science,* 42:2080-2087, 2002.
Sperotto, *Planta* 230:985, 2009.
Stalker et al., *Science* 242:419-422, 1988.
Sullivan et al., *Mol. Gen. Genet.* 215(3):431-440, 1989.
Sutcliffe, *Proc. Natl. Acad. Sci. USA* 75:3737-3741, 1978.
Tang et al., *Genes Dev.* 17: 49-63, 2003.
Thimm et al., *Plant J.* 37:914-39, 2004.
Thomas et al., *Plant Sci.* 69:189-198, 1990.
Thompson et al., *EMBO J.* 6(9):2519-2523, 1987.
Thompson et al., *Euphytica* 85(1-3):75-80, 1995.
Tian et al., *Plant Cell Rep.* 16:267-271, 1997.
Tingay et al., *Plant J.* 11(6):1369-1376, 1997.
Tomes et al., *Plant. Mol. Biol.* 14(2):261-268, 1990.
Torbet et al., *Crop Science* 38(1):226-231, 1998.
Torbet et al., *Plant Cell Reports* 14(10):635-640, 1995.
Toriyama et al., *Theor Appl. Genet.* 73:16, 1986.
Trotochaud et al., *Science* 289: 613-617, 2000.
Tsukada et al., *Plant Cell Physiol.* 30(4)599-604, 1989.
Tsukaya, *Int J Dev Biol* 49: 547-555, 2005.
Twell et al., *Plant Physiol.* 91:1270-1274, 1989.
Van Eck et al., *Plant Cell Reports* 14(5):299-304, 1995.
Vasil et al., *Plant Physiol.* 91:1575-1579, 1989.
Vogel et al., *Arch. Biochem. Biophys.* 401:164-172, 2002.
Vollbrecht et al., *Nature* 350: 241-243, 1991.
von Arnim et al., *Gene* 221:35, 1998.
Waites and Hudson, *Development* 121: 2143-2154, 1995.
Waites et al., *Cell* 93: 779-789, 1998.
Walker et al., *Proc. Natl. Acad. Sci. USA,* 84:6624-6628, 1987.
Wang et al., *Molec. Cell. Biol.* 12(8):3399-3406, 1992.
Xu et al., *Acta Bot Sin* 44: 1194-1202, 2002.
Xu et al., *Cell Res* 17: 512-519, 2007.
Xu et al., *Development* 130: 4097-4107, 2003.
Yamada et al., *Plant Cell Rep.* 4:85, 1986.
Yang and Russell, *Proc. Natl. Acad. Sci. USA* 87:4144-4148, 1990.
Yu et al., *New Phytol.* 143:299-304, 1999.
Zheng and Edwards, *J. Gen. Virol.* 71:1865-1868, 1990.
Zhong and Ye, *Plant Cell Physiol.* 45: 369-385, 2004.
Zukowsky et al., *Proc. Natl. Acad. Sci. USA* 80:1101-1105, 1983.
Zuo et al., *Plant J.* 24:265, 2000.

What is claimed is:

1. An expression cassette comprising a polynucleotide molecule comprising a sequence selected from the group consisting of:
   (a) a sequence encoding SEQ ID NO: 2 or a polypeptide at least 98% identical to SEQ ID NO: 4, wherein the polypeptide regulates plant leaf senescence;
   (b) a sequence comprising SEQ ID NO: 1 or 3; and
   (c) a sequence complementary to the full length of (a) or (b),
   the expression cassette further comprising a heterologous promoter functional in plants operably linked to the polynucleotide molecule.

2. The expression cassette of claim 1, wherein the polynucleotide molecule comprises the sequence of SEQ ID NO:1 or SEQ ID NO:3.

3. A recombinant vector comprising the expression cassette of claim 1.

4. The recombinant vector of claim 3, further comprising at least one additional sequence chosen from the group consisting of: a regulatory sequence, a selectable marker, a leader sequence and a terminator.

5. The recombinant vector of claim 4, wherein the additional sequence is heterologous to the polynucleotide molecule.

6. The recombinant vector of claim 3, wherein the promoter is a tissue-specific promoter.

7. The recombinant vector of claim 3, wherein the promoter directs expression in leaf tissue.

8. A transgenic plant comprising the expression cassette of claim 1.

9. The transgenic plant of claim 8, further defined as a dicotyledonous plant.

10. The transgenic plant of claim 8, further defined as a poplar, a willow, a eucalyptus, a hemp, a *Medicago* sp., a *Lotus* sp., a *Trifolium* sp., a *Melilotus* sp., a *Vinca* sp., a *Glycine* sp., a *Nicotiana* sp., a *Vitis* sp., an *Arabidopsis* sp. or a *Ricinus* sp.

11. The transgenic plant of claim 8, further defined as a monocotyledonous plant.

12. The transgenic plant of claim 8, further defined as a rice, a wheat, a barley, a maize, a switchgrass, an oat, a sugarcane, a rye or a sorghum.

13. The transgenic plant of claim 8, further defined as an $R_0$ transgenic plant.

14. The transgenic plant of claim 8, further defined as a progeny plant of any generation of an $R_0$ transgenic plant, wherein the transgenic plant has the nucleic acid molecule from the $R_0$ transgenic plant.

15. A seed of the transgenic plant of claim 8, wherein the seed comprises the expression cassette.

16. The seed of claim 15, wherein nitrogen content is increased relative to that found in seed of an otherwise isogenic plant lacking the recombinant.

17. A host cell transformed with the recombinant vector of claim 3.

18. The host cell of claim 17, wherein said host cell is a plant cell.

19. A method of altering the distribution of one or more nutrients in a plant, the method comprising growing the plant, wherein the plant comprises the expression cassette of claim 1, wherein the selected sequence is expressed and alters the distribution of one or more nutrients in the plant when compared to an otherwise isogenic plant that lacks the polynucleotide molecule.

20. The method of claim 19, wherein the one or more nutrients comprises protein.

21. The method of claim 19, wherein the plant is an $R_0$ transgenic plant.

22. The method of claim 19, wherein the plant is a progeny plant of any generation of an $R_0$ transgenic plant, wherein the transgenic plant comprises the polynucleotide molecule.

23. The method of claim 19, wherein the altered distribution of one or more nutrients is a decrease of one or more nutrients in the leaves.

24. The method of claim 19, wherein the plant has altered development or morphology when compared to an otherwise isogenic plant that lacks the polynucleotide molecule.

25. The method of claim 24, wherein the altered development is altered leaf senescence.

26. A method of producing plant biomass, the method comprising:
   (a) obtaining the plant of claim 8;
   (b) growing said plant under plant growth conditions to produce plant tissue from the plant; and
   (c) preparing biomass from said plant tissue.

27. The method of claim 26, wherein preparing biomass comprises harvesting said plant tissue.

28. The method of claim 26, further comprising using the biomass for biofuel.

* * * * *

SEQUENCE LISTING

```
<160> NUMBER OF SEQ ID NOS: 22

<210> SEQ ID NO 1
<211> LENGTH: 1104
<212> TYPE: DNA
<213> ORGANISM: Panicum virgatum
<220> FEATURE:
<221> NAME/KEY: CDS
<222> LOCATION: (1)..(1104)
```

<400> SEQUENCE: 1

```
atg acg agc tcg act aga ctg cct aat ctt cca gct ggg ttc cgc ttc      48
Met Thr Ser Ser Thr Arg Leu Pro Asn Leu Pro Ala Gly Phe Arg Phe
1               5                   10                  15 cac ccc aca gat gag gag ctc atc gtc cac tac ctc atg aac caa gct      96
His Pro Thr Asp Glu Glu Leu Ile Val His Tyr Leu Met Asn Gln Ala
            20                  25                  30 tcc tcc atc cca tgc cct gtc ccc atc gtc gcc gag gtc aac atc tac      144
Ser Ser Ile Pro Cys Pro Val Pro Ile Val Ala Glu Val Asn Ile Tyr
        35                  40                  45 cag tgc aac cca tgg gat ctt cct gcc aaa gct ttg ttt gga gag aac      192
Gln Cys Asn Pro Trp Asp Leu Pro Ala Lys Ala Leu Phe Gly Glu Asn
    50                  55                  60 gag tgg tac ttc ttc agc ccg agg gat cgc aag tac ccc aac ggc gcc      240
Glu Trp Tyr Phe Phe Ser Pro Arg Asp Arg Lys Tyr Pro Asn Gly Ala
65                  70                  75                  80 cgc ccc aac cgc gcc gcc gga tcc ggc tac tgg aag gcc acc ggc acc      288
Arg Pro Asn Arg Ala Ala Gly Ser Gly Tyr Trp Lys Ala Thr Gly Thr
                85                  90                  95 gac aag gcc atc ctg ttg act ccg acg agc gag aac atc gga gtc aag      336
Asp Lys Ala Ile Leu Leu Thr Pro Thr Ser Glu Asn Ile Gly Val Lys
            100                 105                 110 aag gcc ctt gtg ttc tac ggc ggt aag cct ccc aag ggt gtc aag aca      384
Lys Ala Leu Val Phe Tyr Gly Gly Lys Pro Pro Lys Gly Val Lys Thr
        115                 120                 125 gac tgg atc atg cac gag tac cgc ctc aca gga gct aac aag aac acc      432
Asp Trp Ile Met His Glu Tyr Arg Leu Thr Gly Ala Asn Lys Asn Thr
    130                 135                 140 aag cgt aga gga tcc tcc atg agg ctg gac gac tgg gtc ctc tgc agg      480
Lys Arg Arg Gly Ser Ser Met Arg Leu Asp Asp Trp Val Leu Cys Arg
145                 150                 155                 160 atc cac aag aag agc aac aat ttt cag ttg tct gat cag gac cag gag      528
Ile His Lys Lys Ser Asn Asn Phe Gln Leu Ser Asp Gln Asp Gln Glu
                165                 170                 175 ggc tcc act gtg gag gaa gaa tcc ctc aac aac aag atg aat gtc aca      576
Gly Ser Thr Val Glu Glu Glu Ser Leu Asn Asn Lys Met Asn Val Thr
            180                 185                 190 att aca gcc tcg ccc aag tct gaa gcc aat aat gat ggt cat gat cat      624
Ile Thr Ala Ser Pro Lys Ser Glu Ala Asn Asn Asp Gly His Asp His
        195                 200                 205 cag ttc cat ccg acg acg atg gcc atg aac aag tca tac tca atc acc      672
Gln Phe His Pro Thr Thr Met Ala Met Asn Lys Ser Tyr Ser Ile Thr
    210                 215                 220 gat ctc ctc aac acc atc gac tac tcg gcg ctc tcg cag ttc ctc gat      720
Asp Leu Leu Asn Thr Ile Asp Tyr Ser Ala Leu Ser Gln Phe Leu Asp
225                 230                 235                 240 gcc cca gct gaa cct gaa cca ccg cta atc tac cca aca aca aca caa      768
Ala Pro Ala Glu Pro Glu Pro Pro Leu Ile Tyr Pro Thr Thr Thr Gln
                245                 250                 255 aca cat cac gaa gca cta ctt aac tac aac aac tac gtg aac aat agc      816
Thr His His Glu Ala Leu Leu Asn Tyr Asn Asn Tyr Val Asn Asn Ser
            260                 265                 270 cac ttc aat ttg cca caa gta gac gca tat tca gat cat gtt gcg act      864
His Phe Asn Leu Pro Gln Val Asp Ala Tyr Ser Asp His Val Ala Thr
        275                 280                 285 aat tgc aac ggt ctg aag agg aag cga gtg atg act atg gat ggt gct      912
Asn Cys Asn Gly Leu Lys Arg Lys Arg Val Met Thr Met Asp Gly Ala
    290                 295                 300
```

```
gaa tcc tcc ttc gac gat gat ggc agc agt aac ttc agt aga aaa cta    960
Glu Ser Ser Phe Asp Asp Asp Gly Ser Ser Asn Phe Ser Arg Lys Leu
305                 310                 315                 320 ctg aag ctg cca agt gat tca agg agc agc agc cac agc cat ttt ggc   1008
Leu Lys Leu Pro Ser Asp Ser Arg Ser Ser Ser His Ser His Phe Gly
                325                 330                 335 agc acg acg agc agc tac tgc aac cag cag ctt gtg gac aca agt ggt   1056
Ser Thr Thr Ser Ser Tyr Cys Asn Gln Gln Leu Val Asp Thr Ser Gly
                340                 345                 350 ttt cag tac agc agc gtg ctg agc tat cca ttc ctc gag atg cag tag   1104
Phe Gln Tyr Ser Ser Val Leu Ser Tyr Pro Phe Leu Glu Met Gln
                355                 360                 365
```

<210> SEQ ID NO 2
<211> LENGTH: 367
<212> TYPE: PRT
<213> ORGANISM: Panicum virgatum

<400> SEQUENCE: 2

```
Met Thr Ser Ser Thr Arg Leu Pro Asn Leu Pro Ala Gly Phe Arg Phe
1               5                   10                  15

His Pro Thr Asp Glu Glu Leu Ile Val His Tyr Leu Met Asn Gln Ala
                20                  25                  30

Ser Ser Ile Pro Cys Pro Val Pro Ile Val Ala Glu Val Asn Ile Tyr
                35                  40                  45

Gln Cys Asn Pro Trp Asp Leu Pro Ala Lys Ala Leu Phe Gly Glu Asn
            50                  55                  60

Glu Trp Tyr Phe Phe Ser Pro Arg Asp Arg Lys Tyr Pro Asn Gly Ala
65                  70                  75                  80

Arg Pro Asn Arg Ala Ala Gly Ser Gly Tyr Trp Lys Ala Thr Gly Thr
                85                  90                  95

Asp Lys Ala Ile Leu Leu Thr Pro Thr Ser Glu Asn Ile Gly Val Lys
                100                 105                 110

Lys Ala Leu Val Phe Tyr Gly Gly Lys Pro Pro Lys Gly Val Lys Thr
                115                 120                 125

Asp Trp Ile Met His Glu Tyr Arg Leu Thr Gly Ala Asn Lys Asn Thr
            130                 135                 140

Lys Arg Arg Gly Ser Ser Met Arg Leu Asp Asp Trp Val Leu Cys Arg
145                 150                 155                 160

Ile His Lys Lys Ser Asn Asn Phe Gln Leu Ser Asp Gln Asp Gln Glu
                165                 170                 175

Gly Ser Thr Val Glu Glu Glu Ser Leu Asn Asn Lys Met Asn Val Thr
                180                 185                 190

Ile Thr Ala Ser Pro Lys Ser Glu Ala Asn Asn Asp Gly His Asp His
            195                 200                 205

Gln Phe His Pro Thr Thr Met Ala Met Asn Lys Ser Tyr Ser Ile Thr
    210                 215                 220

Asp Leu Leu Asn Thr Ile Asp Tyr Ser Ala Leu Ser Gln Phe Leu Asp
225                 230                 235                 240

Ala Pro Ala Glu Pro Glu Pro Pro Leu Ile Tyr Pro Thr Thr Thr Gln
                245                 250                 255

Thr His His Glu Ala Leu Leu Asn Tyr Asn Asn Tyr Val Asn Asn Ser
                260                 265                 270

His Phe Asn Leu Pro Gln Val Asp Ala Tyr Ser Asp His Val Ala Thr
            275                 280                 285

Asn Cys Asn Gly Leu Lys Arg Lys Arg Val Met Thr Met Asp Gly Ala
```

```
                290                 295                 300
Glu Ser Ser Phe Asp Asp Gly Ser Ser Asn Phe Ser Arg Lys Leu
305                 310                 315                 320

Leu Lys Leu Pro Ser Asp Ser Arg Ser Ser His Ser His Phe Gly
                325                 330                 335

Ser Thr Thr Ser Ser Tyr Cys Asn Gln Gln Leu Val Asp Thr Ser Gly
                340                 345                 350

Phe Gln Tyr Ser Ser Val Leu Ser Tyr Pro Phe Leu Glu Met Gln
                355                 360                 365

<210> SEQ ID NO 3
<211> LENGTH: 1113
<212> TYPE: DNA
<213> ORGANISM: Panicum virgatum
<220> FEATURE:
<221> NAME/KEY: CDS
<222> LOCATION: (1)..(1113)

<400> SEQUENCE: 3
```

| | | | | | | | | | | | | | | | | |
|---|---|---|---|---|---|---|---|---|---|---|---|---|---|---|---|---|
| atg | ccg | agc | gcg | act | agc | aga | cta | ccc | aat | ctt | cca | gct | ggg | ttc | cgc | 48 |
| Met | Pro | Ser | Ala | Thr | Ser | Arg | Leu | Pro | Asn | Leu | Pro | Ala | Gly | Phe | Arg | |
| 1 | | | | 5 | | | | | 10 | | | | | 15 | | |
| ttc | cac | ccc | aca | gat | gag | gag | ctc | atc | gtc | cac | tac | ctc | atg | aac | caa | 96 |
| Phe | His | Pro | Thr | Asp | Glu | Glu | Leu | Ile | Val | His | Tyr | Leu | Met | Asn | Gln | |
| | | | 20 | | | | | 25 | | | | | 30 | | | |
| gct | tcc | tcc | ctc | cca | tgc | cct | gtc | ccc | atc | atc | gcc | gag | gtc | aac | atc | 144 |
| Ala | Ser | Ser | Leu | Pro | Cys | Pro | Val | Pro | Ile | Ile | Ala | Glu | Val | Asn | Ile | |
| | | 35 | | | | | 40 | | | | | 45 | | | | |
| tac | cag | tgc | aac | cca | tgg | gac | ctt | cct | gcc | aaa | gct | ttg | ttt | gga | gag | 192 |
| Tyr | Gln | Cys | Asn | Pro | Trp | Asp | Leu | Pro | Ala | Lys | Ala | Leu | Phe | Gly | Glu | |
| | 50 | | | | | 55 | | | | | 60 | | | | | |
| aac | gag | tgg | tac | ttc | ttc | agc | ccc | agg | gat | cgc | aag | tac | ccc | aac | ggc | 240 |
| Asn | Glu | Trp | Tyr | Phe | Phe | Ser | Pro | Arg | Asp | Arg | Lys | Tyr | Pro | Asn | Gly | |
| 65 | | | | | 70 | | | | | 75 | | | | | 80 | |
| gcc | cgc | ccc | aac | cgt | gcc | gcc | gga | tcc | ggc | tac | tgg | aag | gcc | acc | ggc | 288 |
| Ala | Arg | Pro | Asn | Arg | Ala | Ala | Gly | Ser | Gly | Tyr | Trp | Lys | Ala | Thr | Gly | |
| | | | | 85 | | | | | 90 | | | | | 95 | | |
| acc | gac | aag | gcc | atc | ctg | ttg | act | cca | acg | agc | gag | aac | atc | gga | gtc | 336 |
| Thr | Asp | Lys | Ala | Ile | Leu | Leu | Thr | Pro | Thr | Ser | Glu | Asn | Ile | Gly | Val | |
| | | | 100 | | | | | 105 | | | | | 110 | | | |
| aag | aaa | gcc | ctt | gtg | ttc | tat | ggt | ggt | aag | cct | ccc | aag | ggg | gtc | aag | 384 |
| Lys | Lys | Ala | Leu | Val | Phe | Tyr | Gly | Gly | Lys | Pro | Pro | Lys | Gly | Val | Lys | |
| | | | 115 | | | | | 120 | | | | | 125 | | | |
| aca | gac | tgg | atc | atg | cac | gag | tac | cgc | ctc | aca | gga | gct | aac | aag | acc | 432 |
| Thr | Asp | Trp | Ile | Met | His | Glu | Tyr | Arg | Leu | Thr | Gly | Ala | Asn | Lys | Thr | |
| | 130 | | | | | 135 | | | | | 140 | | | | | |
| acc | aag | cgt | aga | gga | tct | tcc | atg | agg | ctg | gac | gac | tgg | gtc | ctc | tgc | 480 |
| Thr | Lys | Arg | Arg | Gly | Ser | Ser | Met | Arg | Leu | Asp | Asp | Trp | Val | Leu | Cys | |
| 145 | | | | | 150 | | | | | 155 | | | | | 160 | |
| agg | atc | cac | aag | aag | agc | aac | aat | ttt | cag | ttc | tct | gac | aag | gac | cag | 528 |
| Arg | Ile | His | Lys | Lys | Ser | Asn | Asn | Phe | Gln | Phe | Ser | Asp | Lys | Asp | Gln | |
| | | | | 165 | | | | | 170 | | | | | 175 | | |
| gag | ggc | tca | act | gtg | gag | gag | gaa | gaa | tcc | ctc | aac | aac | aac | atg | atg | 576 |
| Glu | Gly | Ser | Thr | Val | Glu | Glu | Glu | Glu | Ser | Leu | Asn | Asn | Asn | Met | Met | |
| | | | 180 | | | | | 185 | | | | | 190 | | | |
| aat | ggc | aca | att | gca | gcc | tcg | ccc | aag | tct | gaa | gcc | aat | gat | gat | cat | 624 |
| Asn | Gly | Thr | Ile | Ala | Ala | Ser | Pro | Lys | Ser | Glu | Ala | Asn | Asp | Asp | His | |
| | | 195 | | | | | 200 | | | | | 205 | | | | |
| gat | cat | cag | ttc | cat | ccg | acg | acg | atg | acg | atg | acc | atg | agc | aag | tca | 672 |
| Asp | His | Gln | Phe | His | Pro | Thr | Thr | Met | Thr | Met | Thr | Met | Ser | Lys | Ser | |

```
                210                 215                 220
tac tca atc acc gat cta ctc aac acc atc gac tac tcg gcg ctc tca    720
Tyr Ser Ile Thr Asp Leu Leu Asn Thr Ile Asp Tyr Ser Ala Leu Ser
225                 230                 235                 240 cag ctc ctc gat gcc cca gct gaa cct gaa cca ccg cta atc tac cca    768
Gln Leu Leu Asp Ala Pro Ala Glu Pro Glu Pro Pro Leu Ile Tyr Pro
                245                 250                 255 ata aca aca caa aca cac gaa tca cta ctt agc tat aac aac gac agc    816
Ile Thr Thr Gln Thr His Glu Ser Leu Leu Ser Tyr Asn Asn Asp Ser
            260                 265                 270 cac tac ttc aat ttg cca caa gta gac gca tgt tca gat cat gtt gcg    864
His Tyr Phe Asn Leu Pro Gln Val Asp Ala Cys Ser Asp His Val Ala
        275                 280                 285 cct aat tgc aac ggt ctg aag agg aag cga gtg atg acc atg gat ggt    912
Pro Asn Cys Asn Gly Leu Lys Arg Lys Arg Val Met Thr Met Asp Gly
    290                 295                 300 gct gaa tcc tct gcc ttg gat ggt agc agc agt agt aac ttc agt aga    960
Ala Glu Ser Ser Ala Leu Asp Gly Ser Ser Ser Ser Asn Phe Ser Arg
305                 310                 315                 320 aaa ctg aag ctg cca agt gat tca ata aga agc agc agc cac agc cat   1008
Lys Leu Lys Leu Pro Ser Asp Ser Ile Arg Ser Ser Ser His Ser His
                325                 330                 335 ttt ggc agc acg acg agc agc tac tgc aac cag caa cag ctt gtg gac   1056
Phe Gly Ser Thr Thr Ser Ser Tyr Cys Asn Gln Gln Gln Leu Val Asp
            340                 345                 350 aga agt ggt ttt cag tac agc agc ctg ctg agc tat cca ttc ctc gag   1104
Arg Ser Gly Phe Gln Tyr Ser Ser Leu Leu Ser Tyr Pro Phe Leu Glu
        355                 360                 365 atg cag tag                                                        1113
Met Gln
    370

<210> SEQ ID NO 4
<211> LENGTH: 370
<212> TYPE: PRT
<213> ORGANISM: Panicum virgatum

<400> SEQUENCE: 4

Met Pro Ser Ala Thr Ser Arg Leu Pro Asn Leu Pro Ala Gly Phe Arg
1               5                   10                  15

Phe His Pro Thr Asp Glu Glu Leu Ile Val His Tyr Leu Met Asn Gln
            20                  25                  30

Ala Ser Ser Leu Pro Cys Pro Val Pro Ile Ile Ala Glu Val Asn Ile
        35                  40                  45

Tyr Gln Cys Asn Pro Trp Asp Leu Pro Ala Lys Ala Leu Phe Gly Glu
    50                  55                  60

Asn Glu Trp Tyr Phe Phe Ser Pro Arg Asp Arg Lys Tyr Pro Asn Gly
65                  70                  75                  80

Ala Arg Pro Asn Arg Ala Ala Gly Ser Gly Tyr Trp Lys Ala Thr Gly
            85                  90                  95

Thr Asp Lys Ala Ile Leu Leu Thr Pro Thr Ser Glu Asn Ile Gly Val
        100                 105                 110

Lys Lys Ala Leu Val Phe Tyr Gly Gly Lys Pro Pro Lys Gly Val Lys
    115                 120                 125

Thr Asp Trp Ile Met His Glu Tyr Arg Leu Thr Gly Ala Asn Lys Thr
130                 135                 140

Thr Lys Arg Arg Gly Ser Ser Met Arg Leu Asp Asp Trp Val Leu Cys
145                 150                 155                 160
```

```
Arg Ile His Lys Lys Ser Asn Phe Gln Phe Ser Asp Lys Asp Gln
            165                 170                 175

Glu Gly Ser Thr Val Glu Glu Glu Ser Leu Asn Asn Met Met
            180                 185                 190

Asn Gly Thr Ile Ala Ala Ser Pro Lys Ser Glu Ala Asn Asp Asp His
            195                 200                 205

Asp His Gln Phe His Pro Thr Thr Met Thr Met Thr Met Ser Lys Ser
210                 215                 220

Tyr Ser Ile Thr Asp Leu Leu Asn Thr Ile Asp Tyr Ser Ala Leu Ser
225                 230                 235                 240

Gln Leu Leu Asp Ala Pro Ala Glu Pro Glu Pro Pro Leu Ile Tyr Pro
            245                 250                 255

Ile Thr Thr Gln Thr His Glu Ser Leu Leu Ser Tyr Asn Asn Asp Ser
            260                 265                 270

His Tyr Phe Asn Leu Pro Gln Val Asp Ala Cys Ser Asp His Val Ala
            275                 280                 285

Pro Asn Cys Asn Gly Leu Lys Arg Lys Arg Val Met Thr Met Asp Gly
            290                 295                 300

Ala Glu Ser Ser Ala Leu Asp Gly Ser Ser Ser Asn Phe Ser Arg
305                 310                 315                 320

Lys Leu Lys Leu Pro Ser Asp Ser Ile Arg Ser Ser His Ser His
            325                 330                 335

Phe Gly Ser Thr Thr Ser Ser Tyr Cys Asn Gln Gln Gln Leu Val Asp
            340                 345                 350

Arg Ser Gly Phe Gln Tyr Ser Ser Leu Leu Ser Tyr Pro Phe Leu Glu
            355                 360                 365

Met Gln
    370

<210> SEQ ID NO 5
<211> LENGTH: 807
<212> TYPE: DNA
<213> ORGANISM: Arabidopsis thaliana
<220> FEATURE:
<221> NAME/KEY: CDS
<222> LOCATION: (1)..(807)

<400> SEQUENCE: 5 atg gaa gta act tcc caa tct acc ctc cct cca ggg ttc aga ttt cat      48
Met Glu Val Thr Ser Gln Ser Thr Leu Pro Pro Gly Phe Arg Phe His
1               5                   10                  15 cct acc gac gaa gaa ctc atc gtt tac tat ctt cga aac cag acc atg      96
Pro Thr Asp Glu Glu Leu Ile Val Tyr Tyr Leu Arg Asn Gln Thr Met
                20                  25                  30 tct aaa cca tgc cct gtc tcc atc atc cca gaa gtt gat atc tac aaa     144
Ser Lys Pro Cys Pro Val Ser Ile Ile Pro Glu Val Asp Ile Tyr Lys
            35                  40                  45 ttc gac cca tgg caa tta ccc gag aaa aca gag ttt gga gaa aat gag     192
Phe Asp Pro Trp Gln Leu Pro Glu Lys Thr Glu Phe Gly Glu Asn Glu
        50                  55                  60 tgg tat ttc ttc agc cct aga gaa aga aaa tat cca aac gga gtc aga     240
Trp Tyr Phe Phe Ser Pro Arg Glu Arg Lys Tyr Pro Asn Gly Val Arg
65                  70                  75                  80 cca aac cgg gca gct gtt tcc ggt tat tgg aaa gca acc ggt aca gac     288
Pro Asn Arg Ala Ala Val Ser Gly Tyr Trp Lys Ala Thr Gly Thr Asp
                85                  90                  95 aaa gcc att cac agc ggt tca agt aac gta ggt gtc aag aaa gct cta     336
```

```
Lys Ala Ile His Ser Gly Ser Ser Asn Val Gly Val Lys Lys Ala Leu
                100                 105                 110 gtc ttc tac aaa ggt aga cct cct aaa gga atc aaa act gac tgg atc      384
Val Phe Tyr Lys Gly Arg Pro Pro Lys Gly Ile Lys Thr Asp Trp Ile
            115                 120                 125 atg cat gag tat cgt ctc cat gat tca cgt aaa gca tca acg aaa cgt      432
Met His Glu Tyr Arg Leu His Asp Ser Arg Lys Ala Ser Thr Lys Arg
130                 135                 140 aac ggt tcc atg agg tta gat gaa tgg gta ctg tgt agg ata tac aag      480
Asn Gly Ser Met Arg Leu Asp Glu Trp Val Leu Cys Arg Ile Tyr Lys
145                 150                 155                 160 aag aga gga gca agt aag ctt ctg aat gag caa gag ggt ttc atg gac      528
Lys Arg Gly Ala Ser Lys Leu Leu Asn Glu Gln Glu Gly Phe Met Asp
                165                 170                 175 gaa gta cta atg gag gat gag aca aaa gtt gta gtt aac gaa gca gag      576
Glu Val Leu Met Glu Asp Glu Thr Lys Val Val Val Asn Glu Ala Glu
            180                 185                 190 aga aga act gaa gaa gag ata atg atg atg acg tcg atg aaa ctt cca      624
Arg Arg Thr Glu Glu Glu Ile Met Met Met Thr Ser Met Lys Leu Pro
        195                 200                 205 agg acg tgt tcg ctg gct cat ttg ttg gaa atg gat tac atg gga ccc      672
Arg Thr Cys Ser Leu Ala His Leu Leu Glu Met Asp Tyr Met Gly Pro
210                 215                 220 gtc tct cac att gat aat ttt agt cag ttc gat cat ctt cat caa cct      720
Val Ser His Ile Asp Asn Phe Ser Gln Phe Asp His Leu His Gln Pro
225                 230                 235                 240 gat tcg gag tct agt tgg ttc ggg gac ctt cag ttt aac caa gac gag      768
Asp Ser Glu Ser Ser Trp Phe Gly Asp Leu Gln Phe Asn Gln Asp Glu
                245                 250                 255 atc tta aac cat cat cgt caa gcg atg ttt aag ttt tag                  807
Ile Leu Asn His His Arg Gln Ala Met Phe Lys Phe
            260                 265

<210> SEQ ID NO 6
<211> LENGTH: 268
<212> TYPE: PRT
<213> ORGANISM: Arabidopsis thaliana

<400> SEQUENCE: 6

Met Glu Val Thr Ser Gln Ser Thr Leu Pro Pro Gly Phe Arg Phe His
1               5                   10                  15

Pro Thr Asp Glu Glu Leu Ile Val Tyr Tyr Leu Arg Asn Gln Thr Met
            20                  25                  30

Ser Lys Pro Cys Pro Val Ser Ile Ile Pro Glu Val Asp Ile Tyr Lys
        35                  40                  45

Phe Asp Pro Trp Gln Leu Pro Glu Lys Thr Glu Phe Gly Glu Asn Glu
    50                  55                  60

Trp Tyr Phe Phe Ser Pro Arg Glu Arg Lys Tyr Pro Asn Gly Val Arg
65                  70                  75                  80

Pro Asn Arg Ala Ala Val Ser Gly Tyr Trp Lys Ala Thr Gly Thr Asp
                85                  90                  95

Lys Ala Ile His Ser Gly Ser Ser Asn Val Gly Val Lys Lys Ala Leu
            100                 105                 110

Val Phe Tyr Lys Gly Arg Pro Pro Lys Gly Ile Lys Thr Asp Trp Ile
        115                 120                 125

Met His Glu Tyr Arg Leu His Asp Ser Arg Lys Ala Ser Thr Lys Arg
    130                 135                 140

Asn Gly Ser Met Arg Leu Asp Glu Trp Val Leu Cys Arg Ile Tyr Lys
145                 150                 155                 160
```

```
                145                 150                 155                 160
Lys Arg Gly Ala Ser Lys Leu Leu Asn Glu Gln Glu Gly Phe Met Asp
                    165                 170                 175

Glu Val Leu Met Glu Asp Glu Thr Lys Val Val Asn Glu Ala Glu
                180                 185                 190

Arg Arg Thr Glu Glu Ile Met Met Thr Ser Met Lys Leu Pro
            195                 200                 205

Arg Thr Cys Ser Leu Ala His Leu Leu Glu Met Asp Tyr Met Gly Pro
        210                 215                 220

Val Ser His Ile Asp Asn Phe Ser Gln Phe Asp His Leu His Gln Pro
225                 230                 235                 240

Asp Ser Glu Ser Ser Trp Phe Gly Asp Leu Gln Phe Asn Gln Asp Glu
                245                 250                 255

Ile Leu Asn His His Arg Gln Ala Met Phe Lys Phe
            260                 265

<210> SEQ ID NO 7
<211> LENGTH: 1958
<212> TYPE: DNA
<213> ORGANISM: Arabidopsis thaliana

<400> SEQUENCE: 7
cgtcatctca tcctaatcct catatctttt aatcctatcc tttttgtccc atgccctata      60
tagtaagtat ataaaattgg cttggtgatg tatatgaaca tatgatgaat catgtgccat     120
ttgaaatata gtaataaaca tgtacacttg tgtaaaatag cttttggggt cttttaattt     180
gttagaatag cattttttaga ttgtccatta acaaggtagt ttcttgaaaa attttaaaag     240
atattcatgc gccacttaat tataacggtt taatgaacaa ttatttgtgg caatagcgaa     300
acaaaatcat gaaattaaca agaataaaca gctaatcatg aacttgtttt ttctcctctt     360
tcccactttg tgctggaacg ttccttcgca tcttgtagta atctcacaaa acccatttttc    420
aagaaacttg tgtccagtct gaattgagcg tgtggagttt tttggacaaa tgtagtaaac    480
aaagatttaa tcacccaatt agggaataat aatgacacca ttagataaga acatgcgtaa    540
ttagtgacat ctaattattg tttaatcaga aatccgccgt ggcgcgtggg tgtatgccct     600
ccacaatcct tatccctaat gacttttat gtgaaaatga cacgtcattc agaagcaaaa      660
aaattggacc ccccaagcct tgtagcatgc cacgtttctt ccaaaattaa gaccaagaat     720
ggtcttcaca ctagttttta tgttatacaa gttctttagt acttctcctt tggattcttt    780
ttaattacta gtttgtttta tgaaaaacgt atgttattga ttattgagat atcagtatta    840
ttatatatgc agtataaagt tattgatgtg tatattttgt catgcaaact atatcgtgga    900
gaaaataatg ttgcttatga cttttgatag ttgggcttac atttggataa tggatagggt    960
agacaaagat aggaggaaag caataatagc gaaatgaaga acgaatattt ggggaaatag   1020
gacaaatgaa tatacttctc tttgaaatgg agattcacct aaattattaa tactaaagcc   1080
atgcaatgca tccaaacaaa tcagtggtca agcacactca attatatgtc cacgaagacc   1140
tttagaatct tcacaaccaa agctatttt ctacgctacc tgataattct gactcaattc    1200
ttcttcataa aacgtataat gaagctttat gaatgattaa ttatagacac aaccggcccct  1260
atctgcgatt tctacaaaca atagaacaca aaactttaaa agttactaca aaataccgaa   1320
ttgactatat atatcatatt atcagtataa acatgattag attgatcatg ttatcagta     1380
atcatgaaag acaaagagtg tgactattgt aaaccaaatt ttagaataaa ataaataatt   1440
```

```
tatcatacta tatacagtat tttgttaagt atatgtcatc caatagtaac attatcattt    1500
aaactgaaaa atgtttcagc tactttaagg aattatagct ttattaaaag tatatactttt   1560 taggtcacgt gtttagaggt gaagaacaat aataattact caataagttc accagtcaca    1620
ctccaacatc ttattcaaat tccttttaaa agcttttaa ccgtggctgt ttgatgacca     1680
tttgacaaaa tttagtatat tagaaaaaaa caataggata gggataatat aggacattag    1740
actattagat ggacaaaatg aagtattatt taattttcca atgtaccaac caataagaaa    1800
gaagtgacgc acagtaaacg acaaaaagct caagcataaa aacccaaacc ttctctgctt    1860
tctaaacatt tcaagaacct tgagaacatc aaaaactaac acagaaagaa aaaaaacagt    1920
tcctgttcta ttagattgtt ttctaaattg tctgaaaa                            1958
```

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
gaaatgaaac aagatacaca aagtcac    27

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9
aagcttcggc ctaagtgtca c    21

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
attttgccga tttcggaac    19

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
actcgtgcat gatccagtyk gt    22

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12 kcggggswgaa gaagtaccac tc    22

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
tcgacctcta caagttcgay cc 22

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
gcgagmagga gtggtacttc tt 22

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
ttagatctat ggcggtaagc tctgc 25

<210> SEQ ID NO 16
<211> LENGTH: 40
<212> TYPE: DNA
<213> ORGANISM: Artificial sequence
<220> FEATURE:
<223> OTHER INFORMATION: Primer

<400> SEQUENCE: 16
taggtcaccc tagtgttttt ttctttcata tttgaatttg 40

<210> SEQ ID NO 17
<211> LENGTH: 185
<212> TYPE: PRT
<213> ORGANISM: Panicum virgatum

<400> SEQUENCE: 17

```
Met Thr Ser Ser Thr Arg Leu Pro Asn Leu Pro Ala Gly Phe Arg Phe
1               5                   10                  15

His Pro Thr Asp Glu Glu Leu Ile Val His Tyr Leu Met Asn Gln Ala
            20                  25                  30

Ser Ser Ile Pro Cys Pro Val Pro Ile Val Ala Glu Val Asn Ile Tyr
        35                  40                  45

Gln Cys Asn Pro Trp Asp Leu Pro Ala Lys Ala Leu Phe Gly Glu Asn
    50                  55                  60

Glu Trp Tyr Phe Phe Ser Pro Arg Asp Arg Lys Tyr Pro Asn Gly Ala
65                  70                  75                  80

Arg Pro Asn Arg Ala Ala Gly Ser Gly Tyr Trp Lys Ala Thr Gly Thr
                85                  90                  95

Asp Lys Ala Ile Leu Leu Thr Pro Thr Ser Glu Asn Ile Gly Val Lys
            100                 105                 110

Lys Ala Leu Val Phe Tyr Gly Gly Lys Pro Pro Lys Gly Val Lys Thr
        115                 120                 125
```

-continued

```
Asp Trp Ile Met His Glu Tyr Arg Leu Thr Gly Ala Asn Lys Asn Thr
130                 135                 140

Lys Arg Arg Gly Ser Ser Met Arg Leu Asp Asp Trp Val Leu Cys Arg
145                 150                 155                 160

Ile His Lys Lys Ser Asn Asn Phe Gln Leu Ser Asp Gln Asp Gln Glu
                165                 170                 175

Gly Ser Thr Val Glu Glu Ser Leu
            180                 185

<210> SEQ ID NO 18
<211> LENGTH: 231
<212> TYPE: PRT
<213> ORGANISM: Triticum turgidum

<400> SEQUENCE: 18

Met Gly Ser Ser Asp Ser Ser Gly Ser Ala Gln Lys Ala Thr Arg
1               5                   10                  15

Tyr His His Gln His Gln Pro Pro Pro Gln Arg Gly Ser Ala Pro
                20                  25                  30

Glu Leu Pro Pro Gly Phe Arg Phe His Pro Thr Asp Glu Glu Leu Val
            35                  40                  45

Val His Tyr Leu Lys Lys Lys Ala Asp Lys Ala Pro Leu Pro Val Asn
        50                  55                  60

Ile Ile Ala Glu Val Asp Leu Tyr Lys Phe Asp Pro Trp Glu Leu Pro
65                  70                  75                  80

Glu Lys Ala Thr Ile Gly Glu Gln Glu Trp Tyr Phe Phe Ser Pro Arg
                85                  90                  95

Asp Arg Lys Tyr Pro Asn Gly Ala Arg Pro Asn Arg Ala Ala Thr Ser
                100                 105                 110

Gly Tyr Trp Lys Ala Thr Gly Thr Asp Lys Pro Ile Leu Ala Ser Gly
            115                 120                 125

Thr Gly Cys Gly Leu Val Arg Glu Lys Leu Gly Val Lys Lys Ala Leu
130                 135                 140

Val Phe Tyr Arg Gly Lys Pro Pro Lys Gly Leu Lys Thr Asn Trp Ile
145                 150                 155                 160

Met His Glu Tyr Arg Leu Thr Asp Ala Ser Gly Ser Thr Thr Ala Thr
                165                 170                 175

Asn Arg Pro Pro Val Thr Gly Gly Ser Arg Ala Ala Ala Ser Leu
                180                 185                 190

Arg Leu Asp Asp Trp Val Leu Cys Arg Ile Tyr Lys Lys Ile Asn Lys
            195                 200                 205

Ala Ala Ala Gly Asp Gln Gln Arg Asn Thr Glu Cys Glu Asp Ser Val
210                 215                 220

Glu Asp Ala Val Thr Ala Tyr
225                 230

<210> SEQ ID NO 19
<211> LENGTH: 183
<212> TYPE: PRT
<213> ORGANISM: Arabidopsis thaliana

<400> SEQUENCE: 19

Met Glu Val Thr Ser Gln Ser Thr Leu Pro Pro Gly Phe Arg Phe His
1               5                   10                  15

Pro Thr Asp Glu Glu Leu Ile Val Tyr Tyr Leu Arg Asn Gln Thr Met
            20                  25                  30
```

-continued

Ser Lys Pro Cys Pro Val Ser Ile Ile Pro Glu Val Asp Ile Tyr Lys
         35                  40                  45

Phe Asp Pro Trp Gln Leu Pro Glu Lys Thr Glu Phe Gly Glu Asn Glu
 50                  55                  60

Trp Tyr Phe Phe Ser Pro Arg Glu Arg Lys Tyr Pro Asn Gly Val Arg
 65                  70                  75                  80

Pro Asn Arg Ala Ala Val Ser Gly Tyr Trp Lys Ala Thr Gly Thr Asp
                 85                  90                  95

Lys Ala Ile His Ser Gly Ser Ser Asn Val Gly Val Lys Lys Ala Leu
            100                 105                 110

Val Phe Tyr Lys Gly Arg Pro Pro Lys Gly Ile Lys Thr Asp Trp Ile
        115                 120                 125

Met His Glu Tyr Arg Leu His Asp Ser Arg Lys Ala Ser Thr Lys Arg
    130                 135                 140

Asn Gly Ser Met Arg Leu Asp Glu Trp Val Leu Cys Arg Ile Tyr Lys
145                 150                 155                 160

Lys Arg Gly Ala Ser Lys Leu Leu Asn Glu Gln Glu Gly Phe Met Asp
                165                 170                 175

Glu Val Leu Met Glu Asp Glu
            180

<210> SEQ ID NO 20
<211> LENGTH: 200
<212> TYPE: PRT
<213> ORGANISM: Solanum lycopersicum

<400> SEQUENCE: 20

Met Glu Ser Thr Asp Ser Ser Thr Gly Thr Arg His Gln Pro Gln Leu
 1               5                  10                  15

Pro Pro Gly Phe Arg Phe His Pro Thr Asp Glu Glu Leu Ile Val His
                 20                  25                  30

Tyr Leu Lys Lys Arg Val Ala Gly Ala Pro Ile Pro Val Asp Ile Ile
            35                  40                  45

Gly Glu Ile Asp Leu Tyr Lys Phe Asp Pro Trp Glu Leu Pro Gly Lys
     50                  55                  60

Ala Ile Phe Gly Glu Gln Glu Trp Phe Phe Phe Ser Pro Arg Asp Arg
 65                  70                  75                  80

Lys Tyr Pro Asn Gly Ala Arg Pro Asn Arg Ala Ala Thr Ser Gly Tyr
                 85                  90                  95

Trp Lys Ala Thr Gly Thr Asp Lys Pro Val Phe Thr Ser Gly Gly Thr
            100                 105                 110

Gln Lys Val Gly Val Lys Lys Ala Leu Val Phe Tyr Gly Gly Lys Pro
        115                 120                 125

Pro Lys Gly Val Lys Thr Asn Trp Ile Met His Glu Tyr Arg Val Val
    130                 135                 140

Glu Asn Lys Thr Asn Asn Lys Pro Leu Gly Cys Asp Asn Ile Val Ala
145                 150                 155                 160

Asn Lys Lys Gly Ser Leu Arg Leu Asp Asp Trp Val Leu Cys Arg Ile
                165                 170                 175

Tyr Lys Lys Asn Asn Thr Gln Arg Ser Ile Asp Asp Leu His Asp Met
            180                 185                 190

Leu Gly Ser Ile Pro Gln Asn Val
        195                 200

<210> SEQ ID NO 21

```
<211> LENGTH: 200
<212> TYPE: PRT
<213> ORGANISM: Oryza sativa

<400> SEQUENCE: 21

Met Val Leu Ser Asn Pro Ala Met Leu Pro Gly Phe Arg Phe His
1               5                   10                  15

Pro Thr Asp Glu Glu Leu Ile Val His Tyr Leu Arg Asn Arg Ala Ala
            20                  25                  30

Ser Ser Pro Cys Pro Val Ser Ile Ile Ala Asp Val Asp Ile Tyr Lys
        35                  40                  45

Phe Asp Pro Trp Asp Leu Pro Ser Lys Glu Asn Tyr Gly Asp Arg Glu
    50                  55                  60

Trp Tyr Phe Phe Ser Pro Arg Asp Arg Lys Tyr Pro Asn Gly Ile Arg
65                  70                  75                  80

Pro Asn Arg Ala Ala Gly Ser Gly Tyr Trp Lys Ala Thr Gly Thr Asp
                85                  90                  95

Lys Pro Ile His Ser Ser Gly Gly Ala Ala Thr Asn Glu Ser Val Gly
            100                 105                 110

Val Lys Lys Ala Leu Val Phe Tyr Lys Gly Arg Pro Pro Lys Gly Thr
        115                 120                 125

Lys Thr Asn Trp Ile Met His Glu Tyr Arg Leu Ala Ala Asp Ala
    130                 135                 140

His Ala Ala Asn Thr Tyr Arg Pro Met Lys Phe Arg Asn Thr Ser Met
145                 150                 155                 160

Arg Leu Asp Asp Trp Val Leu Cys Arg Ile Tyr Lys Lys Ser Ser His
                165                 170                 175

Ala Ser Pro Leu Ala Val Pro Pro Leu Ser Asp His Glu Gln Asp Glu
            180                 185                 190

Pro Cys Ala Leu Glu Glu Asn Ala
        195                 200

<210> SEQ ID NO 22
<211> LENGTH: 183
<212> TYPE: PRT
<213> ORGANISM: Oryza sativa

<400> SEQUENCE: 22

Met Glu Cys Gly Gly Ala Leu Gln Leu Pro Gly Phe Arg Phe His
1               5                   10                  15

Pro Thr Asp Asp Glu Leu Val Met Tyr Tyr Leu Cys Arg Lys Cys Gly
            20                  25                  30

Gly Leu Pro Leu Ala Ala Pro Val Ile Ala Glu Val Asp Leu Tyr Lys
        35                  40                  45

Phe Asn Pro Trp Asp Leu Pro Glu Arg Ala Met Gly Gly Glu Lys Glu
    50                  55                  60

Trp Tyr Phe Phe Ser Pro Arg Asp Arg Lys Tyr Pro Asn Gly Gln Arg
65                  70                  75                  80

Pro Asn Arg Ala Ala Gly Thr Gly Tyr Trp Lys Ala Thr Gly Ala Asp
                85                  90                  95

Lys Pro Val Gly Ser Pro Arg Ala Val Ala Ile Lys Lys Ala Leu Val
            100                 105                 110

Phe Tyr Ala Gly Lys Pro Pro Lys Gly Val Lys Thr Asn Trp Ile Met
        115                 120                 125

His Glu Tyr Arg Leu Ala Asp Val Asp Arg Ser Ala Ala Ala Arg Lys
    130                 135                 140
```

```
Leu Ser Lys Ser Ser His Asn Ala Leu Arg Leu Asp Asp Trp Val Leu
145                 150                 155                 160

Cys Arg Ile Tyr Asn Lys Lys Gly Val Ile Glu Arg Tyr Asp Thr Val
                165                 170                 175

Asp Ala Gly Glu Asp Val Lys
                180
```